US010895562B2

(12) United States Patent
Pratt et al.

(10) Patent No.: US 10,895,562 B2
(45) Date of Patent: Jan. 19, 2021

(54) METHOD AND APPARATUS FOR DETERMINING THE COMPOSITION OF ONE OR MORE GASES

(71) Applicant: HONEYWELL INTERNATIONAL INC., Morris Plains, NJ (US)

(72) Inventors: Keith Francis Edwin Pratt, Portsmouth (GB); Tom Gurd, Eastleigh (GB); Cristian Vasile Diaconu, Bucharest (RO); Martin Geoffrey Jones, Havant (GB)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 190 days.

(21) Appl. No.: 16/160,785

(22) Filed: Oct. 15, 2018

(65) Prior Publication Data

US 2020/0116692 A1   Apr. 16, 2020

(51) Int. Cl.
*G01N 33/00* (2006.01)
*G01N 27/27* (2006.01)

(52) U.S. Cl.
CPC ..... *G01N 33/0062* (2013.01); *G01N 33/0031* (2013.01); *G01N 2033/0068* (2013.01)

(58) Field of Classification Search
CPC ....... G01N 27/00–04; G01N 27/26–27; G01N 33/00; G01N 33/0031; G01N 33/00662; G01N 2033/0068
See application file for complete search history.

(56) References Cited

U.S. PATENT DOCUMENTS

| 5,832,411 A | 11/1998 | Schatzmann et al. |
| 2005/0287043 A1 | 12/2005 | Stromereder et al. |
| 2008/0226505 A1 | 9/2008 | Willettt et al. |
| 2010/0121210 A1 | 5/2010 | Lindner et al. |
| 2010/0219960 A1* | 9/2010 | Moe ............... G01N 33/0032 340/632 |
| 2016/0018373 A1 | 1/2016 | Page et al. |

(Continued)

FOREIGN PATENT DOCUMENTS

| EP | 2581735 A1 | 4/2013 |
| JP | H07-305838 A | 11/1995 |

OTHER PUBLICATIONS

Extended European Search Report for Application No. 19203112.8, dated Mar. 17, 2020, 8 pages.

(Continued)

*Primary Examiner* — Nguyen Q. Ha
(74) *Attorney, Agent, or Firm* — Alston & Bird LLP

(57) ABSTRACT

A method and apparatus are provided to determine the composition of one or more gases. In the context of a method, a sensory assembly and at least one processor, the sensor assembly comprising a first gas sensor and a second gas sensor, includes causing the first sensor to be powered to detect a presence of one or more gas while the second sensor is unpowered. The method further includes detecting the presence of one or more gases while the second sensor is unpowered. In response to detecting the presence of the one or more gases, the method includes causing the second sensor to be powered. The method still further includes capturing sensor data corresponding to at least one of the one or more gases. The method also includes identifying the at least one of the one or more gases based on an analysis of the sensor data.

18 Claims, 9 Drawing Sheets

(56) References Cited

U.S. PATENT DOCUMENTS

2017/0241964 A1* 8/2017 Vereecken .......... G01N 33/004
2017/0248544 A1   8/2017 Pratt et al.
2017/0370891 A1  12/2017 Yoo
2019/0369075 A1* 12/2019 Schwartz ............. G01N 31/22

OTHER PUBLICATIONS

Annex to the communication dated Nov. 6, 2020 for EP Application No. 19203112.8, 4 pages.
Communication Pursuant to Article 94(3) dated Nov. 6, 2020 for EP Application No. 19203112.8, 2 pages.

* cited by examiner

METHOD AND APPARATUS FOR DETERMINING THE COMPOSITION OF ONE OR MORE GASES

TECHNOLOGICAL FIELD

An example embodiment relates generally to a method and associated apparatus and, more particularly, to a method and associated apparatus for detecting and identifying one or more gases.

BACKGROUND

Modern gas sensors come in various forms, which may require burdensome equipment or multiple, distinct sensors for a single work environment. Applicant has identified a number of deficiencies and problems associated with current sensors. For example, many lack the ability to accurately determine the composition of one or more gases, while not using more than a desired amount of power. Through applied effort, ingenuity, and innovation, many of these identified problems have been solved by the methods and apparatus of the present disclosure.

BRIEF SUMMARY

The combination of accuracy and power conservation are both factors to consider in making gas sensors. Many current gas sensors are able to detect a limited number of gases, but give little to no additional information about the composition. In some embodiments, a method for determining the composition of one or more gases with a sensor assembly and at least one processor is provided. The sensor assembly may include a first gas sensor and a second gas sensor. In some embodiments, the method may include causing the first sensor to be powered to detect a presence of one or more gases while the second sensor is unpowered; detecting, via the first sensor, the presence of the one or more gases while the second sensor is unpowered; in response to detecting the presence of the one or more gases, causing the second sensor to be powered; generating, via the second sensor, sensor data corresponding to at least one of the one or more gases; and identifying, via the at least one processor, the at least one of the one or more gases based on an analysis of the sensor data.

In some embodiments, the method may include determining a quantity of total gases present based on first sensor data generated by the first sensor and determining the proportions and identities of the one or more gases based on the sensor data generated by the second sensor. The identities of the at least one of the one or more gases may be determined by comparing voltages at which the second sensor response peaks occur with response peaks of at least one known gas.

In some embodiments, the method may include combining, via the at least one processor, the quantity of total gases present determined from the first sensor data generated by the first sensor with the proportions and identities of the one or more gases determined from the sensor data generated by the second sensor to determine the total amount and identity of one or more of the detected gases.

The second sensor may have a surface area less than that of the first sensor.

In some embodiments, the sensor assembly may include a housing defining a limiting capillary proximate to at least one of the first sensor and the second sensor. The limiting capillary may be configured to limit the volume of one or more gases that the at least one of the first sensor or second sensor receives.

Detecting, via the first sensor, the presence of the one or more gases may include applying a constant voltage to the first sensor and detecting a change in current through the first sensor.

Generating, via the second sensor, the sensor data corresponding to the at least one of the one or more gases may include applying a plurality of voltages to the second sensor and receiving current measurements through the second sensor at each of the plurality of voltages.

Identifying, via the at least one processor, the at least one of the one or more gases based on the analysis of the sensor data may include comparing the received current measurements at each of the plurality of voltages with known measurements of predetermined gases.

In some embodiments the sensor assembly may include a second first sensor. The second first sensor may be configured to cause the second sensor to be powered in response to detecting the presence of a second one or more gases, and the one or more gases may be different than the second one or more gases.

In another example embodiment, an apparatus for determining the composition of one or more gases including a sensor assembly and at least one processor may be provided. The sensor assembly may include a first gas sensor and a second gas sensor. The at least one processor may have computer coded instructions therein, with the computer instructions configured to, when executed, cause the apparatus to cause the first sensor to be powered to detect a presence of one or more gases while the second sensor is unpowered; detect, via the first sensor, the presence of the one or more gases while the second sensor is unpowered; in response to the detection of the presence of the one or more gases, cause the second sensor to be powered; generate, via the second sensor, sensor data corresponding to at least one of the one or more gases; and identify, via the at least one processor, the at least one of the one or more gases based on an analysis of the sensor data.

In some embodiments, the computer instructions may be configured to cause the apparatus to determine a quantity of total gases present based on first sensor data generated by the first sensor and determine the proportions and identities of the one or more gases based on the sensor data generated by the second sensor. The identities of the at least one of the one or more gases may be determined by comparing voltages at which the second sensor response peaks occur with response peaks of at least one known gas.

In some embodiments, the computer instructions may be configured to cause the apparatus to combine the quantity of total gases present determined from the first sensor data captured by the first sensor with the proportions and identities of the one or more gases determined from the sensor data generated by the second sensor to determine the total amount and identity of one or more of the detected gases.

The second sensor may have a surface area less than that of the first sensor.

The apparatus may include a housing defining a limiting capillary proximate to at least one of the first sensor and the second sensor. The limiting capillary may be configured to limit the volume of one or more gases that the at least one of the first sensor or second sensor receives.

In some embodiments, detecting, via the first sensor, the presence of the one or more gases may include applying a constant voltage to the first sensor and detecting a change in current through the first sensor.

In some embodiments, generating, via the second sensor, the sensor data corresponding to the at least one of the one or more gases may include applying a plurality of voltages to the second sensor and receiving current measurements through the second sensor at each of the plurality of voltages.

In some embodiments, identifying, via the at least one processor, the at least one of the one or more gases based on the analysis of the sensor data may include comparing the received current measurements at each of the plurality of voltages with known measurements of predetermined gases.

In some embodiments, the apparatus may include a second first sensor. The second first sensor may be configured to cause the second sensor to be powered in response to detecting the presence of a second one or more gases, and the one or more gases may be different than the second one or more gases.

In some embodiments, the second sensor may be configured to generate the sensor data for each gas capable of detection by the first sensor.

BRIEF DESCRIPTION OF THE DRAWINGS

Figure 1:
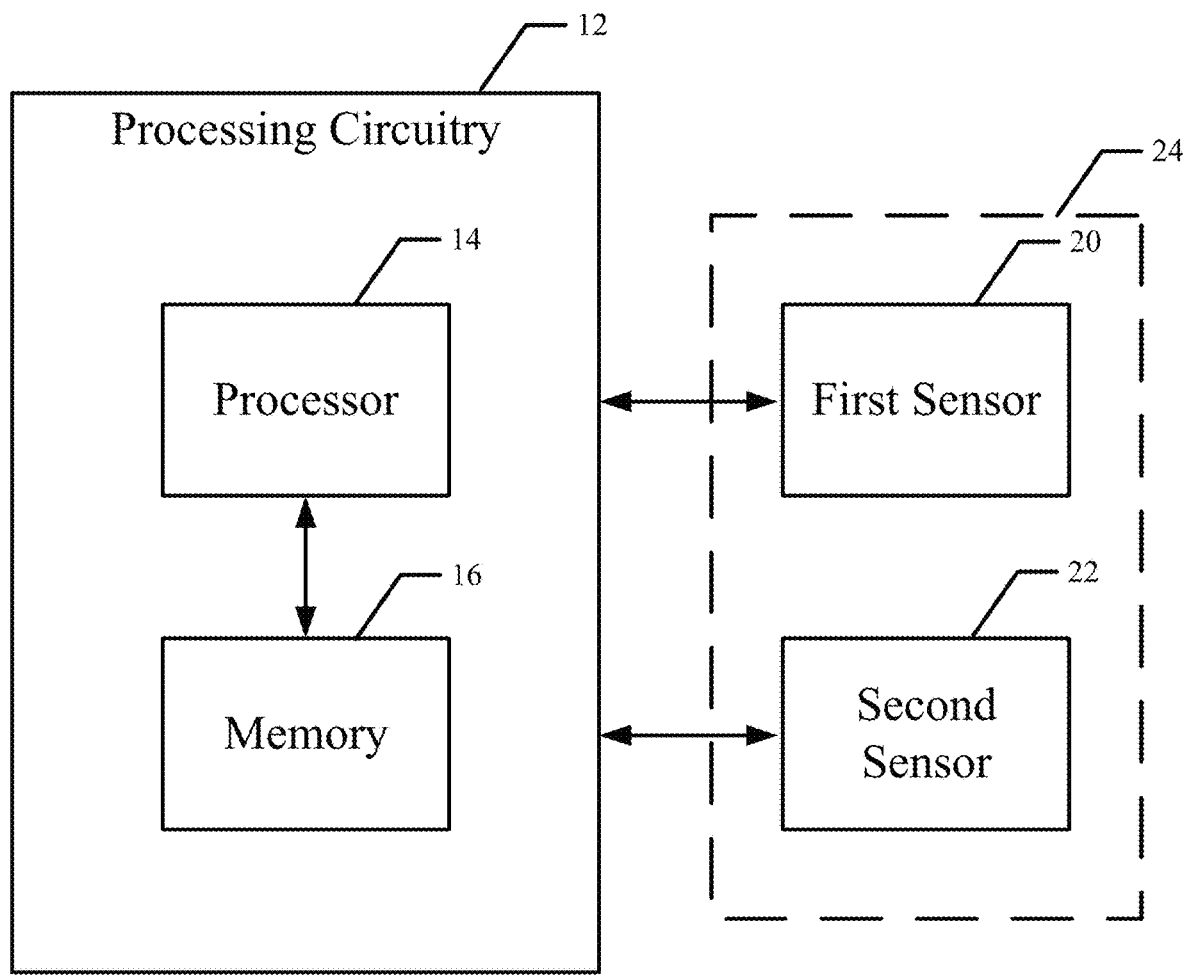
Figure 2:
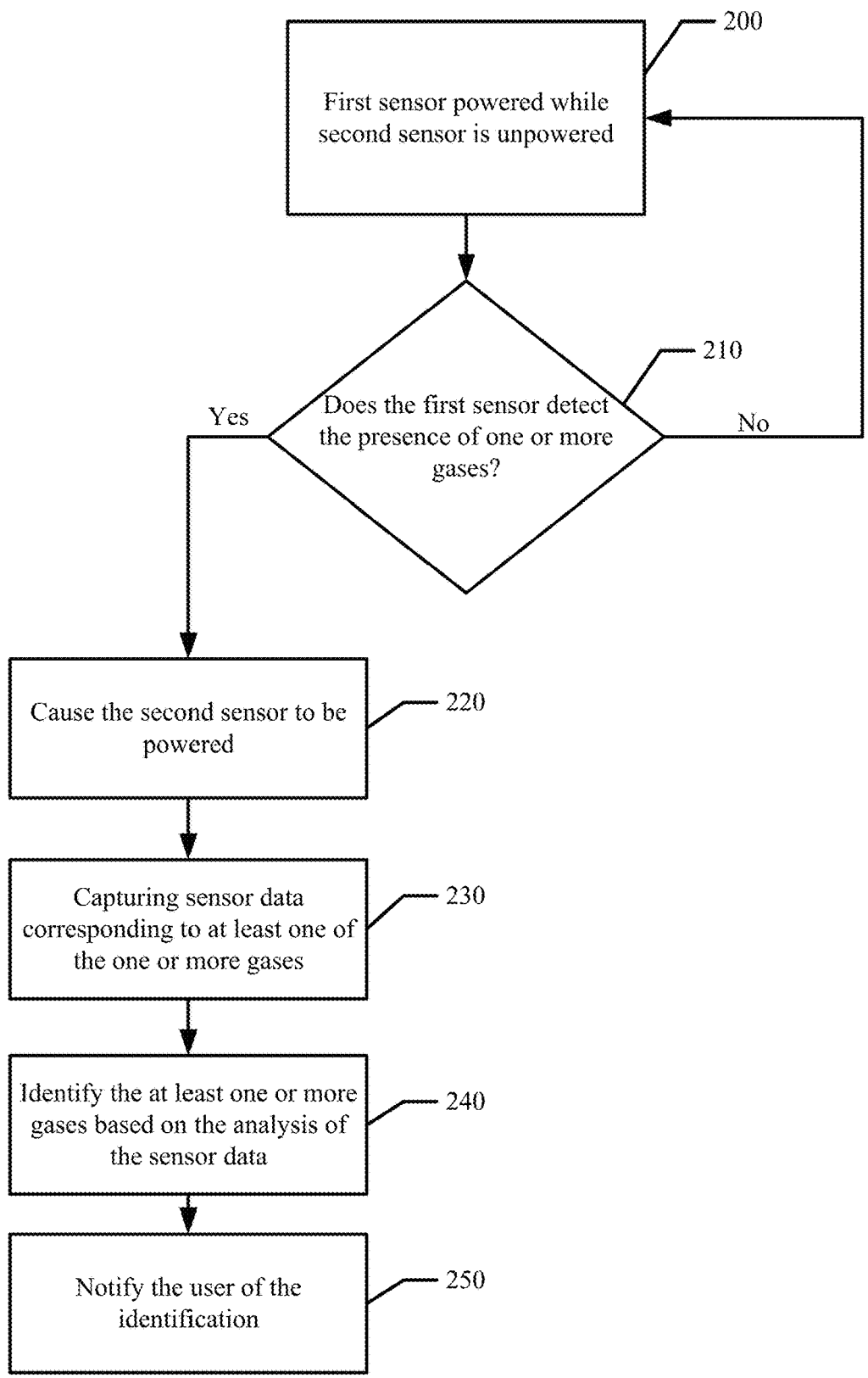
Figure 3:
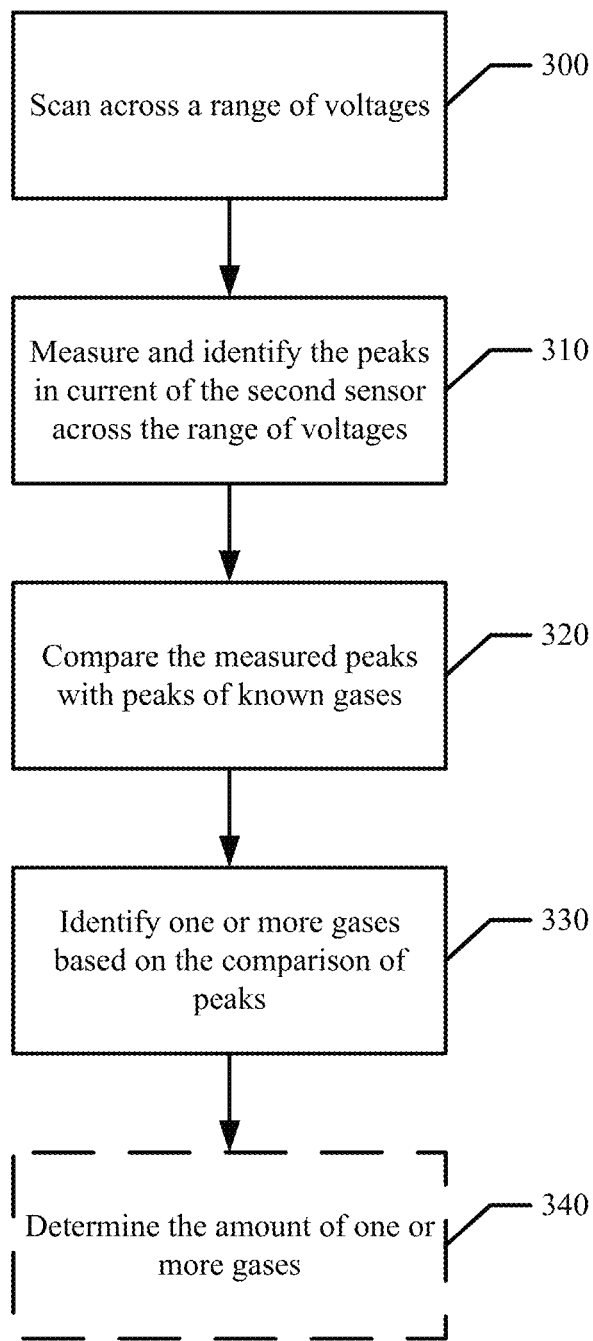
Figure 4:
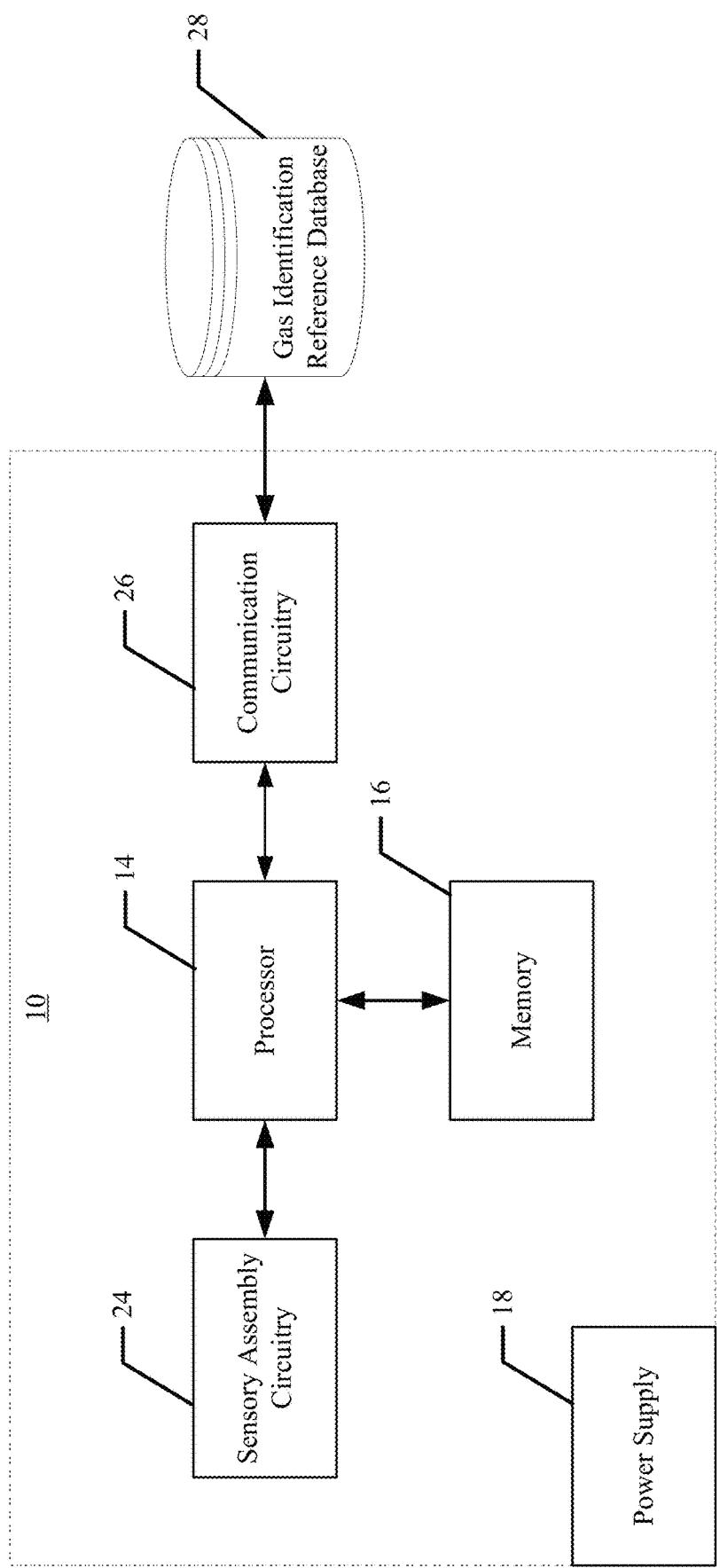
Figure 5:
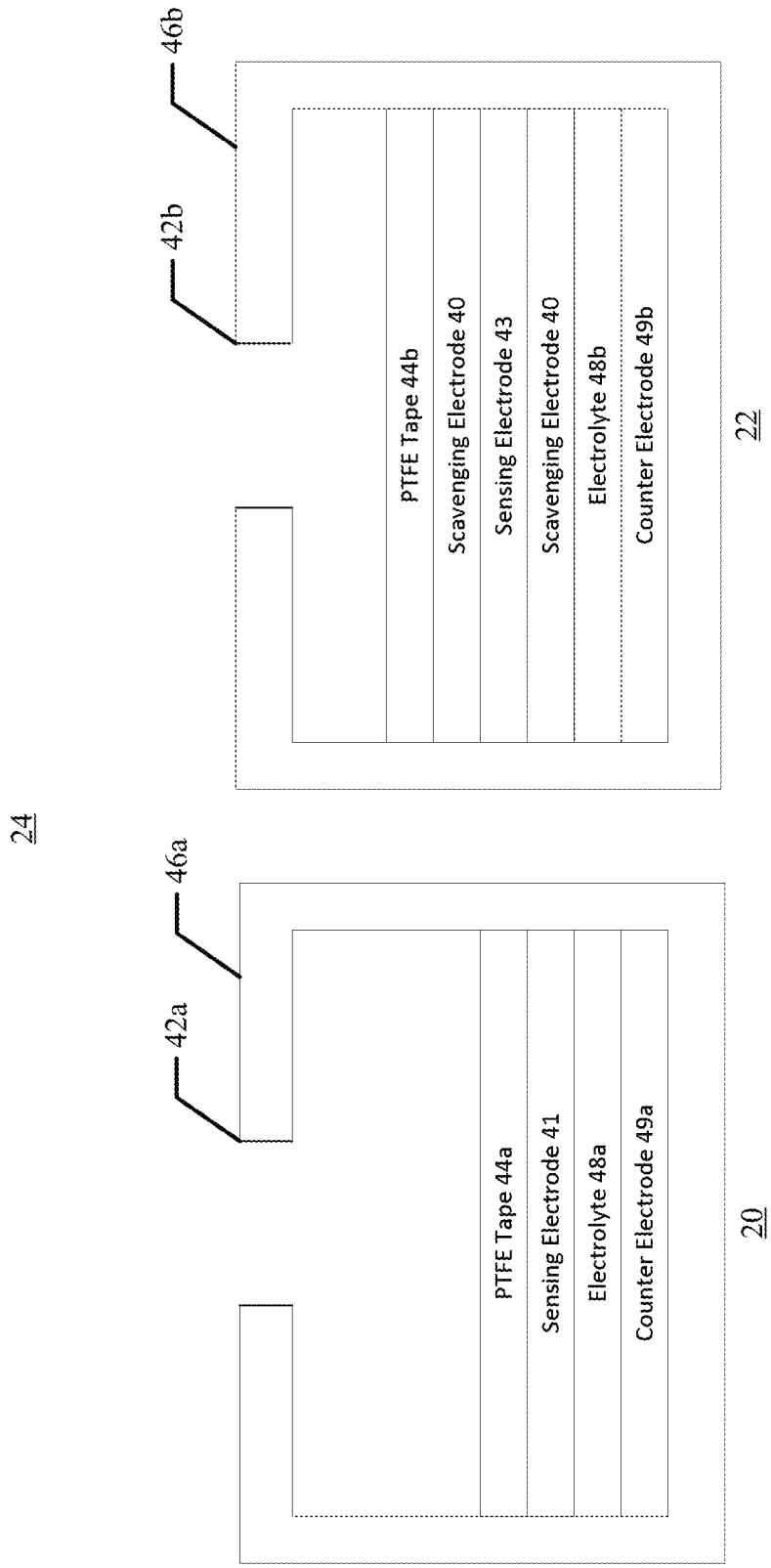
Figure 6:
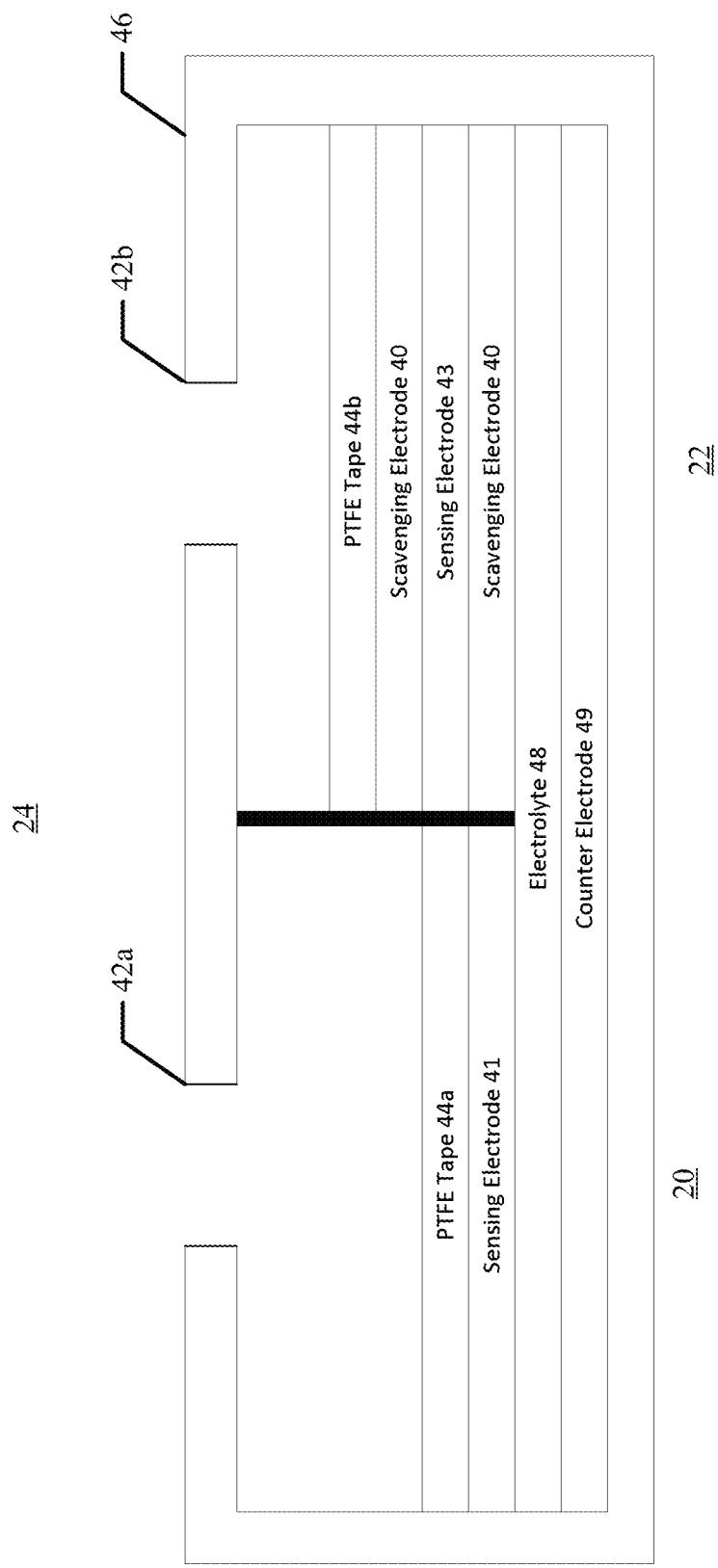
Figure 7:
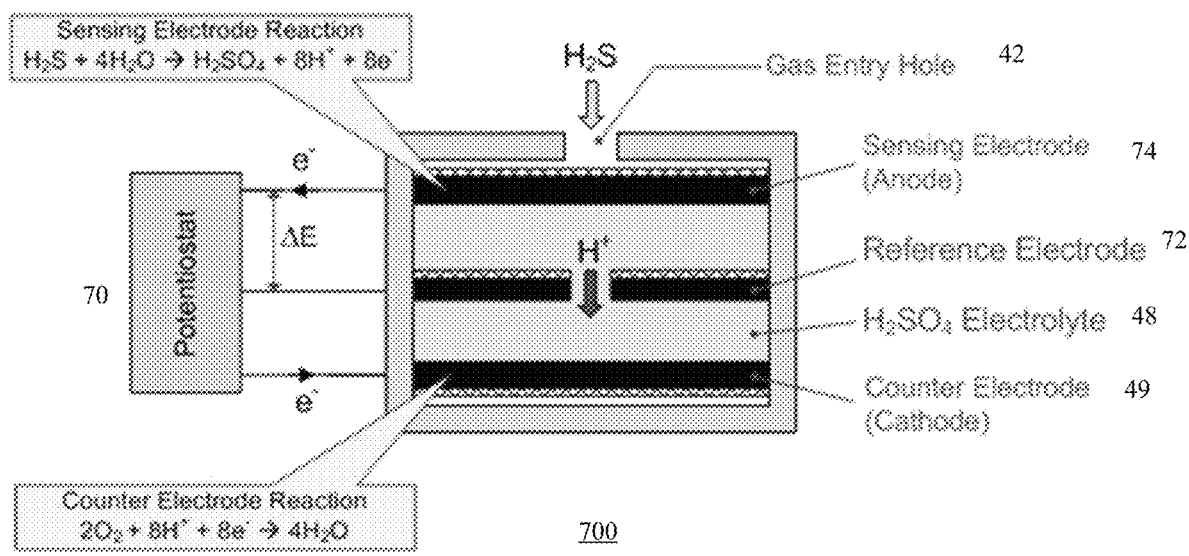
Figure 8:
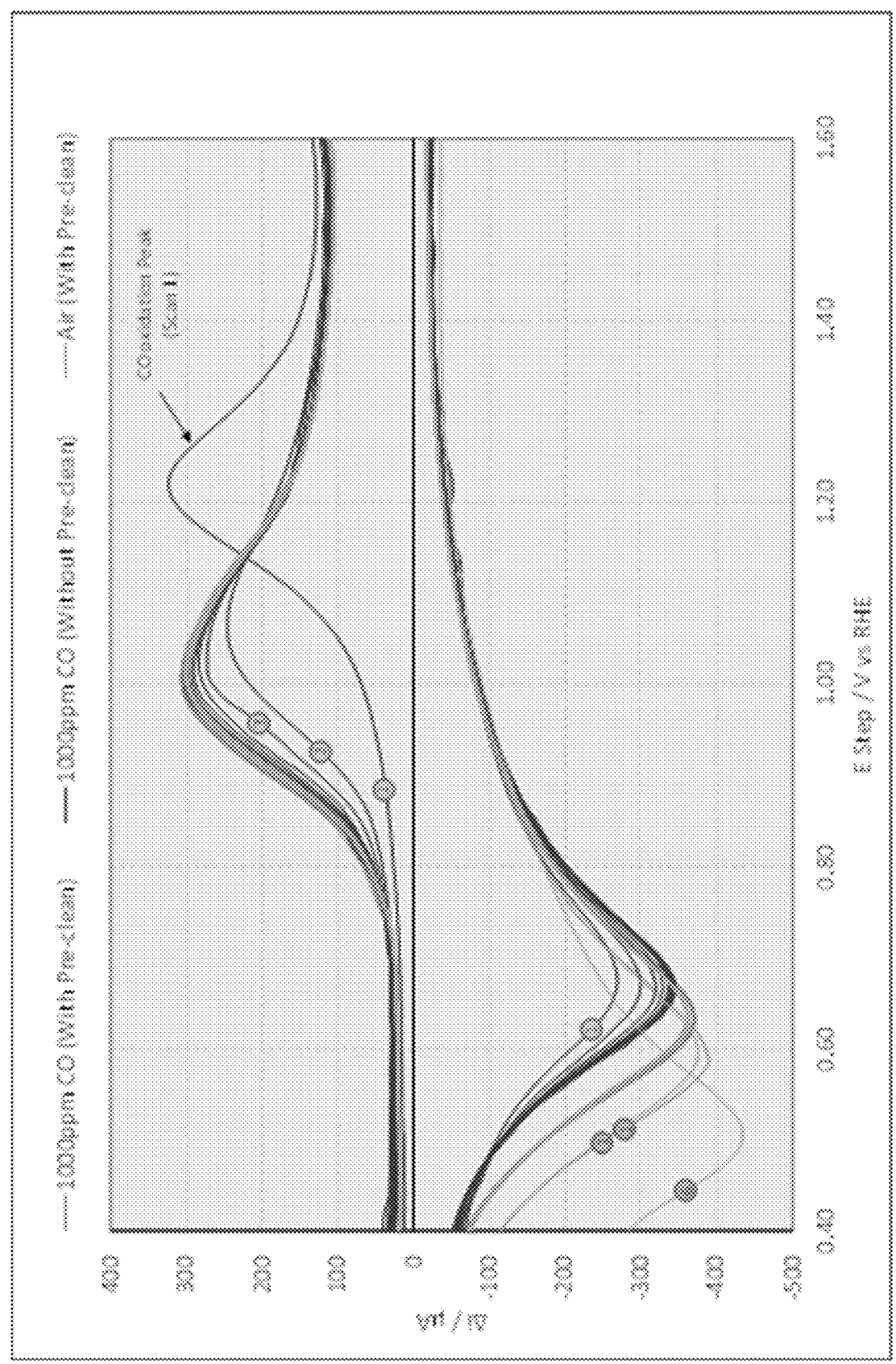
Figure 9:
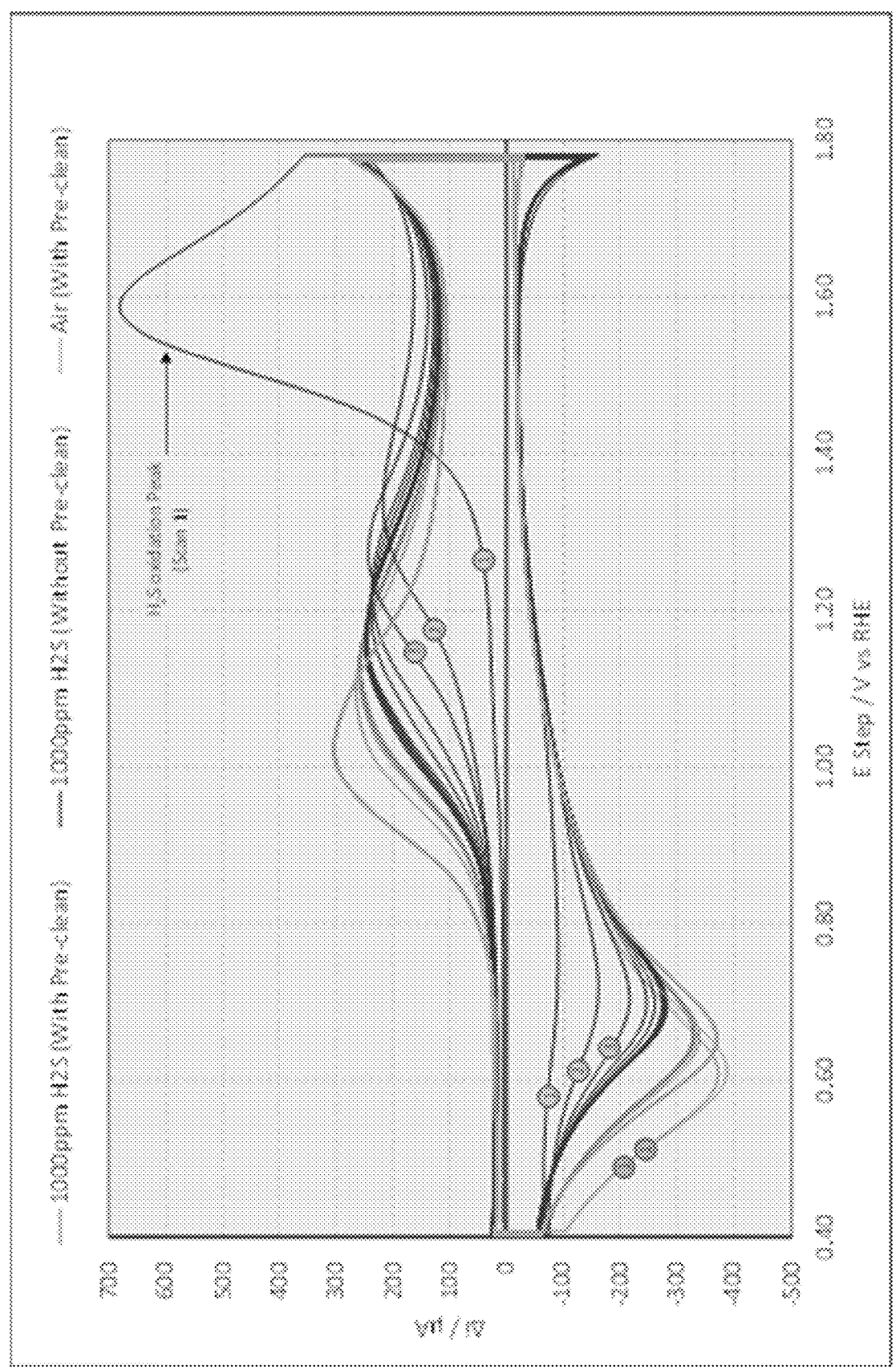

Having thus described certain example embodiments of the present disclosure in general terms, reference will hereinafter be made to the accompanying drawings, which are not necessarily drawn to scale, and wherein:

FIG. 1 is a block diagram of an apparatus configured in accordance with an example embodiment of the present disclosure;

FIG. 2 is a flowchart illustrating the operations performed, such as by the apparatus of FIG. 1, in accordance with an example embodiment of the present disclosure;

FIG. 3 is a further flowchart illustrating a portion of the operations of the present invention, such as Blocks 220 and 230 of FIG. 2, in accordance with an example embodiment of the present disclosure;

FIG. 4 is a block diagram of a system architecture of the present invention in accordance with an example embodiment of the present disclosure;

FIG. 5 is an example embodiment of a sensory assembly, such as the one in FIG. 1, in accordance with an example embodiment;

FIG. 6 is another example embodiment of a sensory assembly, such as the one in FIG. 1, in accordance with an example embodiment;

FIG. 7 is an example embodiment of a gas diffusion sensor used in an example embodiment of the present disclosure;

FIG. 8 is an example plot of current peaks in an identification sensor in an example embodiment of the present disclosure; and FIG. 9 is another example plot of current peaks in an identification sensor in an example embodiment of the present disclosure.

DETAILED DESCRIPTION

Some embodiments will now be described more fully hereinafter with reference to the accompanying drawings, in which some, but not all, embodiments are shown. Indeed, various embodiments may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being generated, processed, transmitted, received, and/or stored in accordance with embodiments of the present disclosure. Thus, use of any such terms should not be taken to limit the spirit and scope of embodiments of the present disclosure.

The present disclosure provides a method and apparatus used to detect and determine the composition of one or more gases. For gas sensors, particularly portable or wearable gas sensors, energy efficiency is an important aspect of the performance and user satisfaction with the device. There is a need for an accurate, high efficiency gas sensor that can detect and differentiate between multiple different gases.

The apparatus described herein in various embodiments may be designed to be used in hazardous conditions. For example, this apparatus may be used for portable safety devices in coal mines, at chemical sites, and/or on oil rigs. Additionally, the apparatus may be used in air monitors that read the ambient air quality. The apparatus may be portable, fixed, or mounted to a mobile platform. In some embodiments, the housing(s) that the apparatus embodies may include a mounting mechanism. One skilled in the art would understand that traditional methods of fixing gas sensors may be used in the present invention.

Some sensors used for detecting gases include gas diffusion electrodes. These gas diffusion electrodes may be large enough to be able to effectively detect certain gases. The particular gas(es) and quantity of gases detected by the electrode are determined based on the voltage applied to the electrode and materials making up the electrode. The size of the electrode contributes to determining the sensitivity of the sensor, with larger electrodes being capable of providing earlier gas detection of smaller concentrations of gas.

Traditional electrodes are also difficult to clean effectively and therefore accuracy can be hampered when attempting to perform multiple scans in quick succession. Moreover, the capacitance of the traditional, larger electrodes prevents scanning across multiple voltages, or otherwise varying the voltage applied to the electrode during operation. Specifically, the charging currents associated with a change in bias voltage swamp the gas signal and therefore make the sensor inaccurate. This problem was historically solved by limiting the effective response range of a sensor to only one or a very small number of possible gases so that each sensor would only respond to a particular desired gas. Thus, when a sensor was triggered, the user would know that the target gas was likely, but not certainly, present because the sensor was incapable of detecting other gases.

Traditionally, sensors of a sufficient size to produce a sufficiently early detection time are operated at a constant voltage and are ill equipped to detect multiple gases. This solution then required the user to carry multiple, discrete sensors each designed to detect a single, different gas. Traditional sensors using gas diffusion electrodes are typically operated in a gas phase diffusion limited manner, whereby the sensitivity of the sensor to gas is controlled by the rate at which the gas can diffuse through a limiter, such as a capillary. This has the advantage that the sensitivity is not dependent on the activity of the electrode, and has a small predictable temperature coefficient, resulting in a more accurate reliable signal.

The inventors have identified that a smaller electrode, such as a microelectrode (e.g., a wire or sputtered electrode) or a smaller gas diffusion electrode, may be used to identify one or more gases by applying multiple voltages to the electrode and recording the response of the gas at the sensor for each voltage. By comparing the responses of the unknown gas with known responses of reference gases at each of the applied voltages, the system may identify each of the gases present and determine the proportion of each gas present. These microelectrodes are much smaller in surface area and therefore the voltage may be varied to collect multiple successive sets of data over a short time without the difficulties of the larger sensors described above. The smaller surface area of these microelectrodes also makes the sensor less sensitive and therefore less likely to be able to detect the total quantity of a gas present and less reliable as a detector in low concentrations of gas. In some embodiments, the low sensitivity of the smaller sensor may cause the sensor to be less reliable for estimating the total quantity of the gases present. Microelectrodes may not have the high surface area and ease of gas access of a gas diffusion electrode, such that running a microelectrode in a gas diffusion limited manner may be impractical. In some embodiments, the absolute sensitivity of a microelectrode may be based on the surface area, activity, cleanliness, and temperature of the electrode.

The apparatus and method of the present disclosure, in an example embodiment, may employ a multi-sensor approach that uses at least two sensors a sensor assembly comprising multiple electrodes) together to provide a lower powered, high accuracy detecting apparatus, where the apparatus provide better performance than the sum of the component sensors.

The apparatus may include a sensor assembly, which has at least a first sensor and a second sensor, and at least one processor. The first sensor may be any device that has the ability to detect one or more gases when powered. The first sensor may be embodied as a detection sensor, which is configured for detecting the presence of gas within the sensor's detection range. In a sample embodiment, the first sensor may be a gas diffusion electrode that is capable of detecting one or more gases.

The second sensor of the at least two sensors may be embodied as an identification sensor, which may be configured for identifying and/or determining the relative proportions of the gases. The second sensor may be any device that has the ability to identify one or more gases when powered, and also may be configured to determine the proportions of the one or more gases.

In an example embodiment, the second sensor may have a smaller surface area than the first sensor to allow multiple scans at varying voltages to occur rapidly. In some embodiments, the second sensor is a gas diffusion electrode. In some embodiments, the second sensor may be a microelectrode. In some embodiments, the microelectrode is made of platinum. In some embodiments, the microelectrode is a platinum wire. In some embodiments, the platinum wire has a length of 1 millimeter (mm). In some embodiments, the platinum wire has a width of 50 micrometers (µm). In some embodiments, the platinum wire has a length of 1 millimeter and diameter of 50 micrometers. In an example embodiment, the first sensor may be powered either intermittently or continuously in order to detect the presence of one or more gases. In some embodiments, the second sensor may only be powered if the first sensor detects one or more gases. The powering of the second sensor may be done using hardware and/or software. A processor may make the determination of when to power the second sensor based on the information received from the first sensor (e.g., the processor operates in lower power mode and is switched into a higher power mode by the detection of gas(es) by the first sensor). Additionally or alternatively, the reaction of the first sensor may cause the second sensor to be powered absent a determination by the processor (e.g., the second sensor and/or processor may be powered automatically based on a response of the first sensor from one or more gases). For example, an analog comparator may detect the signal caused by one or more target gases interacting with the first sensor and wakeup the processor to drive and process the second sensor. Thus the power draw of the second sensor and processor may be reduced by selectively activating the second sensor, and the interaction of the processor(s) with the second sensor, when triggered by the first sensor.

In a sample embodiment, the first, larger, more sensitive sensor may quantify the overall amount of gases present and the second, smaller, voltage-scanning sensor may estimate the relative proportions of the one or more gases present. This may allow for overall quantification of the one or more gases present to be determined.

Example Apparatus Configuration

FIG. 1 is a schematic diagram of an example apparatus configured for performing any of the operations described herein. Apparatus 10 is an example embodiment that may be embodied by or associated with any of a variety of computing devices that include or are otherwise associated with a device configured for providing is advanced sensory features, which may include a sensory assembly 24.

The apparatus 10 may include, be associated with, or may otherwise be in communication with a communication interface (not shown), processor 14, a memory device 16, and a sensory assembly 24. In some embodiments, the processor 14 (and/or co-processors or any other processing circuitry assisting or otherwise associated with the processor) may be in communication with the memory device 16 via a bus for passing information among components of the apparatus. The memory device 16 may be non-transitory and may include, for example, one or more volatile and/or non-volatile memories. In other words, for example, the memory device 16 may be an electronic storage device (for example, a computer readable storage medium) comprising gates configured to store data (for example, bits) that may be retrievable by a machine (for example, a computing device like the processor). The memory device may be configured to store information, data, content, applications, instructions, or the like for enabling the apparatus to carry out various functions in accordance with an example embodiment of the present invention. For example, the memory device could be configured to buffer input data for processing by the processor. Additionally or alternatively, the memory device could be configured to store instructions for execution by the processor.

The processor 14 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. In some embodiments, the processor 14 may be embodied as one or more processing components (e.g., at least one processor) in a single device or distributed across several devices. A multi-core processor may enable multiprocessing within a single physical package. Additionally or alternatively, the processor may include one or more processors configured in tandem via the bus to enable independent execution of instructions, pipelining and/or multithreading. In some embodiments, each electrode may be in electrical communication with a separate processor and/or memory configured to collectively perform the functions described hererin. Portions of the at least one processor 14 may be powered, while other portions of the at least one processor may remain unpowered during some or all of the detection process.

In an example embodiment, the processor 14 may be configured to execute instructions stored in the memory device 16 or otherwise accessible to the processor. Alternatively or additionally, the processor may be configured to execute hard coded functionality. As such, whether configured by hardware or software methods, or by a combination thereof, the processor may represent an entity (for example, physically embodied in circuitry) capable of performing operations according to an embodiment of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform the algorithms and/or operations described herein when the instructions are executed. However, in some cases, the processor may be a processor of a specific device (for example, the computing device) configured to employ an embodiment of the present invention by further configuration of the processor by instructions for performing the algorithms and/or operations described herein. The processor may include, among other things, a clock, an arithmetic logic unit (ALU) and logic gates configured to support operation of the processor.

The apparatus 10 may be equipped with a sensory assembly 24. The sensory assembly 24 may have two or more sensors designed to, when combined by the at least one processor 14, detect, identify, and quantify one or more gases. The sensory assembly may be configured with a first sensor 20 and a second sensor 22. Additional sensors (not shown) may also be combined with the first sensor and the second sensor within the sensory assembly. These sensors may be deposited into a housing that makes up the sensory assembly. Alternatively, the sensory assembly may be embodied as multiple individual sensors in separate housings, which may be in electrical communication with the one or more computing systems discussed herein. The sensors in the sensory assembly may be a combination of at least one detection sensor and at least one identification sensor.

The first sensor 20 may be configured as a detection sensor. As used herein, a detection sensor may be any device that has the ability to detect one or more gases when powered, and need not be able to distinguish between multiple different gases in its detection range. The first sensor 20 may require minimal power to operate and it serves to trigger the second sensor 22 and its corresponding processing circuitry 12. In some embodiments, the first sensor 20 draws no power in the absence of ambient gas. In one example, the first sensor 20 draws 10 uA in 10 ppm $H_2S$, which equates to 30 uW on a 3V power supply. In some embodiments, the first sensor may be capable of detecting the one or more gases by sensing a current change across the electrodes of the sensor caused by a reaction (e.g., an oxidizing or reducing reaction) between gas at the sensor and the electrodes. The first sensor 20 may be electrical, mechanical, electromechanical, electrochemical, or the like.

The first sensor 20 may have a sensing electrode. The first sensor 20 may be configurable in that it detects different gases based on the voltage provided. In some embodiments, the voltage provided to the first sensor may be constant during detection. For example, a platinum gas diffusion sensor may be operated at a constant voltage from 1V vs NHE (normal hydrogen electrode) to 1.5V vs NHE to detect all reducing gases. In some embodiments, a gold gas diffusion electrode may be operated at a constant voltage from 1V vs NHE to 0V vs NHE to detect all oxidizing gases. In some embodiments, a first voltage applied to the first sensor may be between the limits at which the second sensor is operated. The sensor may be embodied as a gas diffusion sensor. The gas diffusion sensor may, when charged at various voltages, across the sensing electrode and a counter electrode, detect one or more gases in the ambient environment surrounding the electrode by reacting to the one or more gases chemically. The sensor may be able to detect various gases based on the choice of electrode, electrolyte, gas filters, and bias voltage.

In some embodiments, the first sensor 20 may be continuously powered. Additionally, in other embodiments, the first sensor may be powered on intermittently to conserve power. In an example embodiment, the material used for the sensing electrode in a detection sensor may be tailored to detect reducing gases. An example material used to detect reducing gases may be platinum. In another example embodiment, the material used for the sensing electrode in a detection sensor may be tailored to detect oxidizing gases. An example material used to detect oxidizing gases may be gold. In some embodiment, there may be multiple detection sensors, for example, the first sensor may be capable of detecting reducing gases, while a third sensor may be capable of detecting oxidizing gases. In this example embodiment, either sensor may be capable of causing the processor 14 to power the second sensor when one or more gases are detected. In some embodiments, as discussed herein, two first sensors may be used, one which is configured to detect oxidizing gases and one which is configured to detect reducing gases.

In an example embodiment, the detection sensor may be a gas diffusion electrode comprising a mixture of catalyst and polytetrafluoroethylene (PTFE) powder, deposited on a PTFE tape. The catalyst materials may include platinum, iridium, ruthenium, gold, silver, carbon, or a mixture thereof. The electrode may have a diameter between 10 millimeters and 30 millimeters. In some embodiments, the electrode catalyst may be deposited in weights of 5 to 60 milligrams per square centimeter, and a PTFE content of 12 wt % to 40 wt %. The PTFE tape may have a porosity between 2 and 3500 Gurley seconds.

The second sensor 22 may be configured as an identification sensor. As used herein, an identification sensor may be any device that has the ability to detect one or more gases when powered. Additionally, the identification sensor may be configured to identify and determine the relative proportions of gases detected. As discussed more completely below, the identification sensor may have a smaller surface area than a detection sensor. As discussed herein, the second, identification sensor may be a microelectrode (e.g., a wire or sputtered electrode as discussed herein) or a smaller gas diffusion electrode. The apparatus may be configured to cause the second, identification sensor to power on after the first sensor detects one or more gases.

In some embodiments, the second sensor may be powered on immediately after the first sensor detects one or more gases. In some embodiments, there may be a delay in time between the detection of one or more gases by the first sensor and the powering on of the second sensor. In some embodiments, a delay between the detecting of the first sensor and the powering of the second sensor may allow sufficient gas to build up in the vicinity of the second electrode and/or sufficient gas to be absorbed onto the second electrode. The delay may be inversely proportional to the signal from the first sensor (e.g., the higher the amount of gases detected by the first sensor, the shorter delay needed for the second sensor to have sufficient gas buildup). In some embodiments, the delay may be up to 5 minutes. The identification and determination of relative proportions by the second sensor may be done through a scan of different voltages across the second sensor and processing of the sensor data received from the second sensor in response to the gases surrounding the sensor.

In some embodiments, the second sensor 22 may include a microelectrode. In those examples, the surface area of the sensing electrode (e.g., a microelectrode) in an identification sensor may be smaller than the surface area of the sensing electrode in a is detection sensor. In some embodiments, the surface area of the electrodes may include all portions of the surface area configured to interact with the detected gas. The size of the second sensor may be configured such that its capacitance does not prohibit scanning voltages across a wide range. In some embodiments, the second sensor may be able to scan across voltages spanning the effective sensing range of the first sensor (e.g., to identify any gas that may trigger a response in the first sensor). In some embodiments, the second sensor may be able to scan across a wider range of voltages than the effective sensing range of the first sensor. In some embodiments, the range scanned by the second sensor may include the full electrochemical window of the electrolyte (e.g., an aqueous electrolyte, such as sulphuric acid, could be scanned from 0V vs NHE to 1.5V vs NHE). In some embodiments, scanning the second sensor across a wider range of voltages than the effective sensing range of the first sensor may electrochemically clean the second electrode while also sensing the desired gases.

In some embodiments, an identification sensor may be in the form of a disc or a wire. The smaller size of an identification sensor may allow for multiple rapid voltage scans to occur in a short amount of time. For example, in a sample embodiment, the second sensor, operating as an identification sensor, is capable of more than 1 scan per second. These scans, including the processing needed to analyze the results, use relatively high amounts of power, ranging in the milliamps, between the scans themselves and the at least one processor's computations. Therefore, scanning cannot effectively be carried out continuously. The present invention uses a lower powered detection sensor (e.g., the first, larger sensor described herein) to indicate when an identification sensor should be powered. This powering may happen immediately after the detection of one or more gases by the detection sensor. Alternatively, there may be a delay in powering the sensor in order for the identification sensor to get enough access to the surrounding gas to accurately analyze it. As discussed above, the delay in time may be up to 5 minutes. In some embodiments, the length of delay may be based on whether a fast response time is needed or based on the concentrations of gases detected. For example, longer times (e.g., 5 minutes or more) might be used for applications where the gas concentrations are low and/or fast responses are not needed (e.g., environmental monitoring applications). In some embodiments, shorter times (e.g., less than 30 seconds) may be used where higher concentrations are present and/or fast response is needed (e.g., portable safety applications). As discussed herein, the time delay could be made inversely proportional to the signal detected on the first electrode. For example the second sensor could be triggered when the integrated charge on the first electrode as reached a certain predetermined level.

As discussed above, in some embodiments, the second sensing electrode may be a microelectrode. The microelectrode may be either a wire or a disc. In an example embodiment, the microelectrode may comprise a platinum wire with a length from 0.1 millimeters to 20 millimeters and a diameter from 10 micrometers to 200 micrometers. The microelectrode may be made out of platinum, gold, ruthenium, rhodium, iridium, palladium, rhenium, osmium, or their alloys with each other or with other metals (e.g., platinum/nickel alloys). In some embodiments, the microelectrode may be attached to the end of an electrochemically passive supporting wire, such as tantalum or niobium or alloys of these (e.g., tantalum tungsten alloy). In some embodiments, the second sensing electrode may include a thin layer of platinum or any of the metals described above, sputtered onto a porous PTFE supporting tape, with an electrode thickness between 0.01 micrometers and 1 micrometers.

Example System Operation

Referring now to FIG. 2, an example embodiment of the present disclosure includes a flow diagram for processing circuitry 12, the processor 14, the sensory assembly 24, or the like, to determine the composition of one or more gases. Referring to Block 200 of FIG. 2, the first sensor, embodied as a detection sensor as described herein, is powered while the second sensor, embodied as an identification sensor as described herein, remains unpowered. The sensors may be powered by various devices, such as either AC or DC power sources (e.g., power supply 18 shown in FIG. 4). The power source may be embodied as a battery. As described herein, a sensor may be caused to be powered either by a controller controlling power supplied to the sensors or by one or more hardware triggers.

When the first sensor 20 is powered, it may be configured to detect multiple gases based on the voltage provided and the materials used for the first sensor. As discussed above, the bias voltage applied to the electrodes of the first sensor may be constant during a particular gas detecting operation. In some embodiments, the apparatus 10 and first sensor 20 may be recalibrated by applying different biasing voltages to the electrodes of the first sensor depending upon the use case. For example, the apparatus 10 may access (either locally or remotely) a database of voltages corresponding to detection of a particular gas or subset of gases and then apply the stored voltage for one gas detecting operation. In some embodiments, the apparatus 10 and first sensor 20 may be is calibrated based on external data, and the voltage adjusted automatically or manually to maximize the response of a target group of gases.

Referring now to Decision Block 210 of FIG. 2, the first sensor, when powered, either does or does not detect the presence of one or more gases. The first sensor may be powered continuously, such that the system remains in a constant loop between blocks 200 and 210 until one or more of the target gases (e.g., gases that cause above a threshold response in the first sensor) are detected. Although depicted as logical block diagram in FIG. 2, the first sensor may be configured to trigger the processor and/or second sensor to power via either hardware (e.g., completing a circuit to the processor and/or second sensor via one or more logic gates or switches) or software (e.g., programmatically determining that gas is present by monitoring the response of the first sensor over time).

In some embodiments, the first sensor may be an electrochemical sensor. For example, in an electrochemical sensor, the sensor detects one or more gases based on the chemical reaction of the sensing elements to the one or more gases. In some embodiments, other sensors may be used to detect the presence of one or more gases with a sensor. For example, in some embodiments, a Metal Oxide sensor, such as tin oxide, may be used. In some embodiments, in light of the present disclosure, any other type of sensor may be used for either the detection sensor or identification sensor, so long as they possessed the ability to either detect or identify one or more gases, respectively. In some embodiments, an electrochemical sensor may require less power than other sensors and may allow for both sensing electrodes to be in the same assembly, sharing the same electrolyte and counter/reference electrodes.

The apparatus may be pre-configured to detect one or more gases or may be configured to vary the types of gases detected between gas detecting operations. The first sensor may be configured to detect any number or type of gases depending on its specific use case. For example, in some embodiments, the first sensor may comprise platinum electrodes, which may react to reducing gases when an anodic voltage is provided. Alternatively, in another example embodiment, the first sensor may comprise gold electrodes, which may react to oxidizing gases when a cathodic voltage is provided. The first sensor may be configured to either directly (e.g., by its configuration of materials and voltage) or indirectly, through a processor, only detect certain gases and may ignore ambient or non-harmful gases also present (e.g., ambient oxygen). When no gases have been detected, the first sensor may remain powered and the second sensor may remain not is powered in accordance with the block 200, 210 loop. Alternatively, the first sensor and the second sensor may not be powered for a period of time before the method begins again at Block 200.

In some embodiments, the first sensor may include platinum electrodes and a sulphuric acid electrolyte, run at an anodic bias voltage, with the first sensor thereby being configured to detect most gases (e.g., CO, $H_2S$, $SO_2$, VOCs, and the like). A platinum sensor in a traditional gas detector would produce excessive noise and false positives due to the wide range of gases detected; however, the present embodiments use the second sensor to leverage the breadth of the first sensor for energy savings while not sacrificing detecting variability. In some embodiments, the first sensor may include platinum electrodes and a sulphuric acid electrolyte, run at an anodic bias voltage to detect only reducing gases. In some embodiments, the first sensor may include platinum electrodes and a sulphuric acid electrolyte, run at a cathodic bias voltage (e.g., <1V vs NI-IE), with the first sensor thereby being configured to respond to oxidizing gases (e.g., NO). In some embodiments, the first sensor may not respond to oxygen (e.g., by using gold electrodes) to avoid the signal being swamped by ambient oxygen. Thus, as described herein, in some embodiments, multiple first electrodes may be used to detect different subsets of a group of target gases (e.g., a first sensor using platinum electrodes and a second first sensor using gold electrodes within the same sensing assembly as a second sensor e.g., three sensors, including the first first sensor, second first sensor, and second sensor) according to the embodiments described herein).

In some embodiments, the electrolyte may include aqueous solutions of sulphuric acid, phosphoric acid, methanesulfonic acid, lithium chloride, or ionic liquids, such as ethyl methyl imidazolium hydrogen sulfate. In some embodiments, any electrolyte that is used in electrochemical sensors may be used with the electrodes of the present disclosure.

In various embodiments, such as shown in Block 220 of FIG. 2, the second sensor is powered when the first sensor detects the presence of one or more gases. The first sensor may cause the second sensor to be powered, either directly, such as by the detection sensors causing a switch to be flipped when one or more gases are detected, or indirectly, such as by the at least one processor being configured to interpret when one or more gases has been detected.

As discussed above, the second sensor may be powered via either hardware is (e.g., completing a circuit to the second sensor via one or more logic gates or switches) or software (e.g., programmatically determining that gas is present by monitoring the response of the first sensor over time). In some embodiments, the second sensor may be powered by the processor determining to cause the second sensor to be powered. In some embodiments, the second sensor may be automatically powered in response to the first sensor detecting the one or more gases. In some embodiments, the second sensor may be powered either concurrent with or sequentially with the processor being powered. The powering of the second sensor may be mechanical or electrical. In some embodiments, the powering of the second sensor may be through the use of a mechanical switch, such as a relay. In some embodiments, the powering of the second sensor may be through the use of an electrical switch, such as a transistor. In some embodiments, the powering of the second sensor may be through the outputting of an appropriate voltage or range of voltages from the processor. The powering of the second sensor may be done in communication with the processor as described herein. The powering of the second sensor may occur as soon as the first sensor detects the presence of one or more gases. In some embodiments, there may be a delay in powering the second sensor after the first sensor detects the presence of one or more of the gases to allow for a sufficient amount of the gas(es) to be absorbed by the second sensor. The delay in powering the second sensor may be based on the integrated charging time of the second sensor. In some embodiments, the powering may occur before the second sensor is fully saturated (e.g., the second sensor may only need a certain amount of gas that is less than full saturation to operate effectively). In some embodiments, the powering occur after the second sensor has sufficient gas to return a measurable signal. In some embodiments, the processor may delay readout of or consideration of data from the second sensor to allow for a sufficient amount of the gas(es) to be absorbed by the second sensor.

Referring now to Block 230 of FIG. 2, the second sensor (e.g., a microelectrode as disclosed herein) may capture sensor data corresponding to at least one of the one or more gases according to any of the processes disclosed herein. As discussed above, in some embodiments the microelectrode may comprise a small platinum wire or disc of about 10 micrometers to 200 micrometers in diameter. This size of microelectrode may have its potential switched or scanned rapidly (e.g., >1 scan across all desired voltages per second) due to low charging currents. In some embodiments, all desired voltages in the scanning range may be scanned within one second. For example, in some embodiments, the voltage may be scanned from 0V vs NHE to 1.5V vs NHE with a scan rate of 5 volts per second.

As discussed further below in reference to FIG. 3, the second sensor may be configured to capture sensor data that allows for the determination of the identity and the relative proportion of at least one of the one or more gases. This sensor data could be either direct or indirect information about the identity and relative proportions of at least one of the one or more gases. This data may include, or may be processed to include, numerical information relating to the effect of the gas on the components of the second sensor. For example, the data may include, or may be processed to include, current measurements that may be aligned with the voltage applied to the electrodes at a given time to determine the response of the sensor to the surrounding gas for each voltage. In some embodiments, the data recorded by the second sensor may include the reference potential of the sensor as described, for example, in U.S. Publication No. 2017/0248544, which application is incorporated by reference herein in its entirety. The data may be further processed into numerical and/or graphical representation of the sensory results (e.g., the current over a range of voltages scanned across the electrodes). For example, in some embodiments, a graph and/or table of the peaks in current of the sensor over a range of voltages may be stored and/or output from the apparatus. In some embodiments, as described herein, the system may output any of the information to the user or may generate a simplified notification alerting the user that an identified gas has been detected over a predetermined threshold.

Referring now to Block 240 of FIG. 2, the sensor data is analyzed in order to identify the at least one of the one or more gases. This analysis, as discussed in more detail below in reference to FIG. 4, may be done by various devices, including at least one processor. The analysis may be based on a comparison of known information about specific gases to the sensor data. For example, in some embodiments, where the sensor data is a measure of current, then the peaks of the measured currents may be compared to the current peaks of known gases. The detection of peaks in current may be detected by a peak detection algorithm or the like, and as discussed herein, the detected peaks may be compared with a known list of target gases, Which may include, but is not limited to, any of the gases discussed herein. FIG. 8 shows an example plot of the peaks in current for scanned voltages with the sensor detecting Carbon Monoxide (CO) due to a higher peak current near 1.20 volts. FIG. 9 shows an example plot of the peaks in current for scanned voltages with the sensor detecting $H_2S$ due to a higher peak in current near 1.6 volts. The known measurements may be stored in a gas identification reference database ("reference database"). This reference database may be either embodied in the apparatus provided, such as stored in the memory device (e.g., memory 16 shown in FIG. 1), or be remote from the apparatus provided (e.g., in a networked server or external storage device). In some embodiments, the reference database may transmit information to the apparatus 10, such as by near field communication (NFC) including, but not limited to, Bluetooth™ communication, or the like, or other longer wireless connections, such as Wi-Fi or LTE.

The reference database may include a predetermined set of measurements for known gases. Additionally or alternatively, the reference database may be updated based on the information received from the present apparatus.

At block 250, after the at least one of the one or more gases is identified, the apparatus may additionally be configured to notify the user of the identification. This may be done, as discussed below in more detail in reference to FIG. 4, using an audio and/or visual notification. In some embodiments, the notification may give information about the gases found including type, amount, or the like. In some embodiments, the apparatus may be configured to notify the user when certain gases are above a desired level, such as when used in hazardous conditions needing quick reactions, with or without immediately identifying the particular gas to the user (e.g., via a siren or visual indicator). In some embodiments, the data relating to the identification may be stored either in the apparatus itself, such as in the memory device, or remotely in a server for future recall and analysis.

Now referring to FIG. 3, a flow chart of operations performed by an apparatus, such as the one in FIG. 1, demonstrates an example embodiment of Blocks 230 and 240 of FIG. 2. Referring to Block 300 of FIG. 3, the second sensor is scanned across a range of voltages. As used herein, the terms "scan" and "scanning" "voltages" may refer to applying a plurality of different voltages to the sensor electrodes sequentially.

The scanning may be performed by continuously varying the voltage between a minimum and maximum voltage or by varying the voltage in an at least partially stepwise fashion across a plurality of discrete voltages from a minimum voltage to a maximum voltage. In either instance, the set of voltages applied to the electrodes may be considered a "range of voltages." The voltages need not be applied in order of magnitude. In some embodiments, the range of voltages may be predetermined. In some embodiments, the range of voltages may be predetermined based on a number of factors including the sensor material, desired gases identified, desired power usage, or the like. In some embodiments, the range of voltages may be customizable based on a number of factors including the sensor material, is desired gases identified, desired power usage, or the like.

An example embodiment of the second sensor may have a scan of voltages ranging from 0 volts to 1.5 volts over a short period of time. If the one or more gases likely to be present are known, a smaller range of voltages may be scanned over the second sensor to target the desired gases. The second sensor may be configured to be able to quickly perform scans in succession. In some embodiments, the scan rate may be 5 volts per second. In some embodiments, the range of scan rates may be from 50 millivolts per second to 50 volts per second depending on the size of the electrode (e.g., smaller electrodes may be scanned at faster rates). In some embodiments, the second sensor may have electrodes with a small surface area (e.g., a microelectrode) that also allows the sensing electrode to quickly be cleaned (e.g., with a scavenging electrode) between scans.

An example embodiment of the present invention includes a scavenging electrode, which may absorb one or more of the gases in order for the second sensor to not become overloaded and therefore have the accuracy harmed. In some embodiments, the scavenging electrodes may operate between measurement cycles of the second sensor. In some embodiments, the scavenging electrode may operate before and/or after the measurement cycles of the electrode (e.g., the scavenging electrode may be powered after the microelectrode has been scanned from 0 to 1.5 volts in order to clean the electrode for subsequent scans and/or before a subsequent scan to ensure the most recent gases are detected during scanning of the second electrode).

In some embodiments, the first sensor and/or the second sensor may be capillary limited according to the structure defined herein to restrict the flow of ambient gas across the sensor electrodes, such that the sensor may be diffusion limited and avoid overwhelming the sensor during operation.

Referring now to Block 310 of FIG. 3, the current across the second sensor may be measured and stored for each of the voltages applied during the scanning. The peaks in current of the second sensor across the range of voltages may then be identified from the collected data. The peaks may correspond to a maximum current or maximum change in current across the range of voltages applied. In some embodiments, at least a portion of the measurements may be collected by the second sensor and the subsequent calculations may be performed by a processor (e.g. processor 14). The amount of data collected relating to the peaks in current may be based on the breadth and timing of each scan of voltage, as shown in Block 300. In some embodiments, the peak detection algorithm may include median filtering approaches and/or other peak detection processes known in the art.

Referring to Block 320 of FIG. 3, the measured peaks may then be compared to the peaks of known gases under the same conditions. The data relating to the known gases may either be directly comparable to the measured values (e.g., the known values may be stored based on the particular sensor, voltage, and materials used), or the processor may transform at least one of the data points from one or more generic datasets based upon calibration information related to the particular second sensor or type of second sensor used.

In some embodiments, the comparison includes receiving, from the reference database, information relating to the measurements of known gases current responses at an electrode) at certain voltages. This may include preloaded information on a predetermined set of known gases or may be created based on the gas types detected by the first sensor. This comparison may be either indirect, comparing relative changes in current, or direct, line-fitting the measurements over changes in voltage.

The number of known gases that may be compared to the measurements may be variable and may be either user-selectable on the apparatus or predetermined based upon the desired function of the sensory assembly. For example, in some embodiments, only one type of gas is desired to be detected and identified, and therefore the measured peaks may only be compared to the data relating to the one desired gas. If more than one gas is desired, such as in an example embodiment where multiple harmful gases may be present (e.g., the sensor apparatus 10 is configured to sense multiple gases either because multiple gases may be present or because the sensor is configured for multiple use cases), the measurements may be compared to known measurements for multiple gases. In some cases, the gases compared may be predetermined, such as in a sensor configured to only detect carbon monoxide, VOCs, etc. In some embodiments, the apparatus may store the information and response properties for the predetermined gases in the memory device and not require any external connections. In some embodiments, the apparatus may retrieve some or all of the information and response properties for the one or more target gases externally (e.g., from an external reference database as described herein. In some embodiments, the target gases to be compared with the second sensor measurements may be determined by a user or by the processor depending on a use case.

Turning to Block 330 of FIG. 3, once the information relating to the known peaks in current of one or more gases has been retrieved, the at least one processor compares the known data with the measured data to determine if the peaks in the measured is data correspond to one or more of the known gases by at least a threshold level of certainty, using one or more statistical comparison techniques known in the art. In an example embodiment, median filtering may be used to detect the peaks in current.

With continued reference to Block 330 of FIG. 3, one or more gases are identified based on the comparison of the measured peaks and the known peaks of at least one gas. After the measured peaks are compared to one or more known set of peaks for given gases, the identity of one or more gases present is determined. These identities may also include the relative proportion of each gas to the total gases present. In some embodiments, this identification may occur for multiple gases and therefore repeat the comparison multiple times. In some embodiments, only one gas is identified, either due to it being the only desired gas or the only gas identifiable. In some embodiments, the relative proportion of gases may be based on the relative peak amplitudes and/or the area under peaks.

In some embodiments, the second sensor may be powered on and the processor and second sensor may be used to determine the identity and proportions of the gases present with no suggestion of a particular target gas being received from the first sensor.

In this manner, the processing load may be minimized by not requiring analysis or monitoring of the first sensor's signals beyond awaiting a trigger signal to power on the second sensor. In some embodiments, a total quantity of gas may also be determined from the first sensor and used in combination with the measurements of the second sensor.

Referring to optional Block 340 of FIG. 3, the at least one processor may be able to determine the amount of each identified gas using a combination of data provided from the first sensor and the second sensor. In an example embodiment, the first sensor may be able to determine the total quantity of the gases present. In some embodiments, the first sensor may not discriminate between the various different gases and may return data corresponding to a total quantity of all gases capable of detecting. For example, as discussed above, the first sensor may have a higher sensitivity and thus a more accurate measurement of the total quantity of gases present. The second sensor may then be able to determine the identity of the one or more gases detected and the relative proportion of those gases. Therefore, the at least one processor may be configured to use this data in order to determine the quantity of each of the one or more detected gases present by multiplying the total quantity of gas by the various proportions of detected gases.

In some embodiments, the second sensor may configured to detect and identify any gas capable of causing a response in the first sensor using the techniques described herein, such that the proportions determined from the second sensor's data correspond to the quantity determined by the first sensor.

For example, in an embodiment in which only one gas is detected, the total quantity determined by the first sensor will simply be the determined quantity of the gas detected by the second sensor. In another example, when three gases are identified, the quantity of each gas ($Q_1$, $Q_2$, $Q_3$) may be determined using a calculation of the quantity of all gases present ($Q_{alt}$), as determined using information from the first sensor, multiplied by the relative proportions of each respective identified gases ($P_1$, $P_2$, $P_3$), as determined using information from the second sensor.

$$Q_{alt} \times P_1 = Q_1$$

$$Q_{alt} \times P_2 = Q_2$$

$$Q_{alt} \times P_3 = Q_3$$

However, additionally or alternatively, the quantity of each gas may be determined by other mathematical ways.

In some embodiments, one or more determination by the processor may be communicated to the user. This communication may be audible and/or visual. In some embodiments, the communication may include information relating to the gas type(s) and/or amount(s) (e.g., a visual display may be provided that presents this information). For example, in some embodiments, an output of the systems and processes described herein may include a display showing gas type(s) and concentration(s). In some embodiments, the communication may be in the form of an alarm, audible and/or visual, that notifies when a certain threshold of gas has been met (e.g., a carbon monoxide sensor may only have an alarm when carbon monoxide is detected above a dangerous level).

Example System Architecture

Now referring to FIG. 4, a detailed schematic of the system architecture of the present disclosure in accordance with some embodiments is provided. In general, the terms computing entity, entity, device, system, and/or similar words used herein interchangeably may refer to, for example, one or more computers, computing entities, desktop computers, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in some embodiments, the apparatus 10 may include at least one processor 14, a memory 16, a power supply 18, communication circuitry 26, and sensory assembly circuitry 24. The apparatus 10 may be configured to execute any of the operations described herein. Although the components are described with respect to functional limitations, it should be understood that the particular implementations necessarily include the use of particular hardware. It should also be understood that certain of the components described herein may include similar or common hardware. For example, two sets of circuitry may both leverage use of the same processor, network interface, storage medium, or the like to perform their associated functions, such that duplicate hardware is not required for each set of circuitry.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the apparatus 10 may provide or supplement the functionality of particular circuitry. For example, the processor 14 may provide processing functionality, the memory 16 may provide storage functionality, the communication circuitry 26 may provide network interface functionality, and the like.

The sensory assembly circuitry 24 is configured to transfer data within the apparatus through the communication circuitry 26. The information may be relating to various measurements taken by the sensory assembly 24 relating to one or more gases. Additionally, the communication circuitry 26 may also be configured to instruct the sensory assembly on when power certain portions of the sensory assembly, such as the second sensor, and what information to obtain or provide to the communication circuitry. The data from the sensory assembly 24 may further be transmitted to the processor 14.

The processor 14 may use the data from the sensory assembly to determine when to power portions of the sensory assembly, such as the second sensor in the apparatus shown in FIG. 1. Additionally, the processor 14 may use the data from the sensory assembly 24 in combination with information from the reference database 28 to determine the amount, proportion, and/or identity of the one or more gases.

As shown in FIG. 4, the apparatus may be linked to a reference database 28. This reference database may have information relating to various known gases and may be used to help identify said gases based on the sensor data captured by the sensory assembly 24. The reference database 28 may be either external, as shown in FIG. 4, or internal to the apparatus itself. For example, in some embodiments, the reference database 28 may be stored in the memory device 16. The reference database 28 may be static. Alternatively, the reference database 28 may be updated, either continuously or intermittently. The reference database 28 may be a compilation of multiple databases relating to various gases. The data may include various current peaks at a range of voltages for individual gases. The information from the reference database may be provided directly to the processor 14 or through the communication circuitry 26.

Communication circuitry 26 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communication circuitry 26 may include a cellular network, an 802.11, 802.16, 802.20, and/or WiMax network. Further, the communication circuitry 26 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the apparatus 10.

The communication circuitry 26 may be any means such as a device or circuitry embodied in either hardware or a combination of hardware and software that is configured to receive and/or transmit data from/to a network and/or any other device, circuitry, or module in communication with the apparatus 10. In this regard, the communication circuitry 26 may include, for example, a network interface for enabling communications with a wired or wireless communication network. For example, the communication circuitry 26 may include one or more network interface cards, antennae, buses, switches, routers, modems, and supporting hardware and/or software, or any other device suitable for enabling communications via a network. Additionally or alternatively, the communication circuitry may include further circuitry for interacting with the antenna(s) to cause transmission of signals via the antenna(s) or to handle receipt of is signals received via the antenna(s).

In some embodiments, the apparatus 10, via the communication circuitry 26, may also perform input/output operations. For example, in some embodiments, the communication circuitry 26 may be configured to output to the client devices and, in some embodiments, to receive an indication of a user input. The communication circuitry 26 may comprise a user interface and may include a display and may comprise a web user interface, a mobile application, a client device, a kiosk, or the like. In some embodiments, the communication circuitry 26 may also include a keyboard, a mouse, a joystick, a touch screen, touch areas, switches, hard or soft keys, a microphone, a speaker (e.g., any device capable of generating an audible response), or other input/output mechanisms known in the art. The processor may be configured to control one or more functions of one or more user interface elements through computer program instructions (e.g., software and/or firmware) stored on a memory accessible to the processor (e.g., memory 16, and/or the like). For example, in some embodiments, a user may be able to select one or more gases that they desire the apparatus 10 to detect or set thresholds of detection for the outputs (e.g., warnings or alerts) of the system.

Additionally, there may be an output of some type to the user when certain gases have been detected. This output may be in the form of visual and/or audible indicators. For example, if the apparatus were being used as a carbon monoxide sensor, then an alarm may go off if the apparatus determines the level of carbon monoxide is above a certain amount. In some embodiments, the output may be a graphical display (e.g., text, graph, chart, LED or other visual output) that indicates the particular gas(es) detected to the user. In some embodiments, the output may include a grid of illuminating LEDs adjacent pre-marked gas types written on the housing of the sensor apparatus 10 to illuminate an LED adjacent one or more of the names of detected gases. In some embodiments, a visual color coding may be used in the graphical display. In some embodiments, an auditory alert may be used. The auditory alert may be generic for any type of detected gas, or may specifically indicate the type of gas detected and identified. In some embodiments, the output may indicate the particular gas detected, and in some embodiments, the output may comprise a generic output signaling danger or another pre-programmed function to the user.

In some embodiments, the apparatus 10 may include a power supply 18 configured to receive power (e.g., internally from one or more batteries or externally from an alternating or direct current power supply) and power the apparatus. In some embodiments, power may be applied to a bus or other circuitry for allowing distribution of power to the various components described herein. In some embodiments, each of the components of the apparatus may be connected to such buses or other circuitry known in the art to facilitate communication and functional control therebetween. As described above and as will be appreciated based on this disclosure, the present invention may be configured in various forms including with portions of the apparatus 10 shown in FIG. 4 being remote from the actual apparatus. In some embodiments, all of the components necessary to detect, identify, and determine the quantity of one or more gases may be integrated into a single housing. In some embodiments, the apparatus may further comprise several housings or components in wired or wireless communication with each other. Thus, the apparatus 10 can be adapted to accommodate a variety of needs and circumstances.

Example Sensory Assembly Embodiments

Now referring to FIG. 5, the sensory assembly 24 of an example embodiment is shown. This example embodiment has two distinct housings 46*a*, 46*b* for the first sensor 20 and the second sensor 22. This may include providing a separate electrolyte 48*a*, 48*b* to each of the first sensor 20 and the second sensor 22. In some embodiments, the electrolytes 48*a*, 48*b* may be the same, and in some embodiments, the electrolytes 48*a*, 48*b* may differ. Additionally, a separate counter electrode 49 may be provided to each of the first sensor 20 and the second sensor 22. In various example embodiments, additional sensors may be provided either in a combined housing with one of the first sensor 20 or second sensor 22, or separate from both. In some embodiments, the power leads may be connected to the electrodes 41, 43, 49*a*, 49*h* to apply the voltages described herein.

Referring to the first sensor 20 of FIG. 5, in some embodiments, a limiting capillary 42*a* may be defined on or near the sensor which limits the amount of gas around the sensor that can reach the first sensing electrode 41. The capillary 42*a* may be built into the housing itself or may be an attachment. The capillary 42*a* may be configured to diffusion limit the sensor and prevent the sensor from being swamped. In some embodiments, one or more filters may be placed over the housing 46*a*, 46*b* to limit entry of gasses thereto. Diffusion limiting the sensors with a capillary 42*a*, 42*b* may allow the response of the sensor to be linearly proportional to gas concentration. In some embodiments, described below, the second sensor 22 may comprise a capillary 42*b* to ensure accurate calculation of the proportions of gases detected, in some embodiments, the second sensor 22 may not include a capillary. In some embodiments, the capillary 42*b* may not cause diffusion limiting when a scavenging electrode 40 is turned off (e.g., during scanning). In some embodiments that use a microelectrode, the second sensor 22 may optionally not include a capillary 42*b* on the second sensor, or the capillary 42*b* may not be diffusion limiting when the scavenging electrode 40 is turned off. In some embodiments, the capillaries may be from 100 micrometers to 2 millimeters in diameter and 1 millimeter to 5 millimeters in length.

In an example embodiment, such as the one shown in FIG. 5, the first sensor 20 may be a detection sensor having the properties described herein. The first sensor 20 may have a sensing electrode 41. As described above, the sensing electrode 41 in the first sensor 20 may be configured to detect the presence of one or more gases. In some embodiments, the electrode 41 may be a gas diffusion electrode operated at a constant voltage. In some embodiments, applying power to the electrodes 41, 49*a* of the first sensor 20 may enable the sensor to detect the one or more gases for which the sensor is configured.

One or all of the sensing elements e.g., electrodes, electrolyte, etc.) in the present invention may be attached via a threaded screwing mechanism to their respective sensors. In some embodiments, PTFE tape 44*a*, 44*b* may be provided to some or all electrodes 41, 43 onto which the electrodes may be deposited. PTFE tape may be a porous, gas permeable tape that does not allow for liquid (e.g., electrolyte) to pass through. The PTFE tape may form a porous membrane between the ambient environment containing the one or more gases and the sensing electrodes. In various embodiments, the PTFE tape may allow the gas to pass through to the electrodes without any electrolyte leaking during the process.

In some embodiments of the present disclosure, as shown in FIG. 5, one or more electrolytes 48*a*, 48*b* may be provided. The one or more electrolytes may support proper cell operation, including reactions for electrochemical sensors. Each sensor may, as shown in FIG. 5, have an individual source of electrolyte. The support provided by the one or more electrolyte may be facilitating the electrical connection between the sensing electrode 41, 43 and the respective counter electrode 49a, 49b. The sensing electrode may have an initial reaction to the ambient gases provided to the sensor and the electrolyte may facilitate the reacted gases getting to the counter electrode. In some embodiments, the electrolyte may facilitate an electrochemical reaction. For example, the reaction of the gas may occur at the interface between the sensing electrode and the electrolyte, and the counter electrode reaction may occur at the interface with the counter electrode and the electrolyte, such that ions move through the electrolyte between the electrodes to complete the circuit. The reactions may include reducing the interference of non-desired gases, such as CO or O in some embodiments. The electrolytes of the present invention may be aqueous, ionic, or the like. The electrolyte may be in liquid or solid form. When a single electrolyte is referenced, this may refer to a distinct unit of electrolyte when in solid form or a distinct reservoir of electrolyte when in liquid form. In some embodiments, the electrolyte may include sulphuric acid, phosphoric acid, methanesulfonic acid, lithium chloride, or ionic liquids, such as ethyl methyl imidazolium hydrogen sulfate. In some embodiments, an ionic electrolyte, may include pure or acid doped and may further comprise one of: 1-ethyl-3-methylimidazolium hydrogensulfate (EMIM.HS), EMIM.HS+methanesulfonic acid (MSA), EMIM.MS, 1-ethyl-3-methylimidazolium methylsulfate (EMIM.MS)+1,2,4-trimethylpyrazolium methylsulfate (TMP.MS), TMP.MS+MSA, TMP.MS+bis (trifluoromethane)sulfonimide (HTFSI), N-n-butyl-N-methylpiperidinium bis(trifluoromethane)sulfonimide (DMEA.TFSI), DMEA.TFSI+MSA, N,N,N',N'-tetraethylsulfamide (TES.TFSI), TES.TFSI+MSA, N,N-dimethylethanolamine bis(trifluoromethane)sulfonimide (DMEA.TFSI), DMEA.TFSI-MSA, DMEA.TFSI+HTFSI, butyldiethanolamine bis(trifluoromethylsulfonyl)imide (BDEA.TFSI), or BDEA.TFSI+HMSA.

In some embodiments, the sensors 20, 22 may include one or more counter electrodes 49a, 49b. The one or more counter electrodes 49a, 49b may be deposited in the housing of one or more sensors during formation. In some embodiments, the counter electrode may react to the resultant ions after the gas has reacted with the sensing electrode. In order to operate correctly, the counter electrode may need access to oxygen. In example embodiments, this oxygen may be provided in either the ambient gas or dissolved in the electrolyte. The oxygen produced by the counter electrode may be used by the sensing electrode to facilitate a reaction with target gases. If too much dissolved oxygen is near the counter electrode, then portions of it may be vented out of the sensor. The oxygen may be consumed or evolved at the counter electrode depending on whether reducing or oxidizing gases are being detected. In some embodiments, the counter electrode 49a, 49h may have an opposite reaction to that of the respective sensing electrode 41, 43 for a given gas (e.g., the sensing electrode may reduce the gas while the counter electrode oxidizes the gas, or vice versa).

In operation, gas diffuses into the sensing electrode 41, 43 where it is oxidized or reduced (e.g., depending upon the anodic or cathodic configuration of the electrode as discussed herein). The reaction causes a current in the apparatus circuitry as detected by a processor which may be detected as the response from the sensor to a given voltage. (The apparatus circuitry a processor) may maintain the voltage across the sensor (e.g., with a potentiostat or the like as discussed herein).

In some embodiments, as shown in FIG. 5, each sensor may have a distinct counter electrode 49a, 49b. Alternatively, some sensors may share a common counter electrode depending on the configuration (e.g., the configuration shown in FIG. 6), The counter electrode may have a negative charge, in example embodiments where the sensing electrode has a positive charge. The current generated based on the potential difference between the sensing electrode and the counter electrode may be used to determine the gases detected by a detection sensor, such as the first sensor 20 in FIG. 5, or the identity and relative proportion for an identification sensor, such as the second sensor 22 in FIG. 5. The counter electrode 49 can comprise a substrate or membrane such as a PTFE membrane, a GEFC-IES membrane, a Nafion® membrane, or the like having a catalytic material disposed thereon. In an embodiment, the catalytic material can be mixed and disposed on the membrane using any suitable process such as rolling, coating, screen printing, or the like to apply the catalytic material on the membrane, as described in more detail herein. The catalyst layer can then be bonded to the membrane through a sintering process.

In an example embodiment, the catalytic material for the counter electrode can comprise a noble metal such as gold (Au), platinum (Pt), ruthenium (Ru), rhodium (Rh), Iridium (Ir), oxides thereof, or any combination thereof. In an embodiment, the catalytic material comprises a platinum ruthenium (Pt—Ru) mixture that is screen printed on the membrane, where the membrane can be a PTFE membrane. In some embodiments, the membrane may be a GEFC-IES membrane. The catalyst loading for the counter electrode 49 can be within any of the ranges described herein for the sensing electrode. In an embodiment, the catalyst loading for the counter electrode 49 can be the same or substantially the same as the catalyst loading for the sensing electrode, the catalyst loading can also be greater than or less than that of the sensing electrode. As also shown in the three-electrode example embodiment of FIG. 7, in order to detect the current and/or potential difference across the electrodes in response to the presence of the target gas, one or more leads or electrical contacts can be electrically coupled to the sensing electrode and/or the counter electrode.

Referring now to the second sensor 22 of FIG. 5, a limiting capillary 42b may be defined on or near the sensor which limits the amount of gas that can reach the sensing electrode 43 in much the same way a limiting capillary is provided to the first sensor. The capillary 42b may be configured to diffusion limit the sensor and prevent the sensor from being swamped. In some embodiments, one or more filters may be placed over the housing 46a, 46h to limit entry of gasses thereto. Diffusion limiting the sensors with a capillary 42a, 42b may allow the response of the sensor to be linearly proportional to gas concentration. In some embodiments, described below, the second sensor 22 may comprise a capillary 42b to ensure accurate calculation of the proportions of gases detected.

In some embodiments, one or more scavenging electrodes 40 may be provided to limit the amount of ambient gas received by the sensing electrode 43 of at least the second sensor 22. The scavenging electrode 40 may be used to limit gases from reaching the sensing electrode at undesired times or quantities and to clean the electrode of any residual dissolved gases after operation of the electrode. For example, the scavenging electrode 40, may be employed to reduce the amount of gas that reaches the sensing electrode in the identification sensor while the second, identification sensor 22 is powered off to prevent overwhelming the sensor 22. In some embodiments, the scavenging electrodes 40 may ensure that the gas analyzed by the second sensor 22 is fresh, and thus the measured proportions are accurate, by removing previously-dissolved gases. Therefore, in some embodiments, the scavenging electrode 40 may be powered continuously or intermittently, even while the identification sensor is not. In some embodiments, the scavenging electrode 40 may be powered on before the second sensor (e.g., identification sensor) is powered, but after the first sensor 20 (e.g., detection sensor) has detected the presence of one or more gases, such as during the delay discussed herein. The scavenging electrode may be constructed using the materials described with respect to the sensing and/or counter electrodes described herein.

In an example embodiment, as shown in FIGS. 5-6, the second sensor may operate as an identification sensor, triggered by the first sensor's detection of one or more gases. The second sensor 22 (identification sensor), as discussed above may have a sensing electrode 43 and a counter electrode 49, 49b. The sensing electrode 43 in the identification sensor may have a smaller surface area than the sensing electrode 41 in the detection sensor. For example, in some embodiments, the sensing electrode 43 may be a microelectrode as discussed above. As described herein, the sensing electrode 43 of the second sensor 22 may be configured to provide sensor data to the at least one processor to enable the processor to determine the identity and relative proportions of at least one of the one or more gases detected by the first sensor 20.

In some example embodiments, such as the one shown in FIGS. 5-6, the first sensor 20 detecting the presence of one or more gases may trigger the power to be supplied to the second sensor for both single housing embodiments (e.g., as shown in FIG. 6) and dual housing embodiments (e.g., as shown in FIG. 5). In this regard, the first sensor 20 to the second sensor 22 may be connected using either a physical or wireless connection. In some embodiments, the first sensor 20 may supply information to the at least one processor (e.g., processor 14 shown in FIG. 1 and FIG. 4), which processor then triggers the power to be supplied to the second sensor. This information may include an indication to the at least one processor that one or more gases has been detected. In some embodiments, the first sensor may provide the at least one processor with sensor data that the processor may monitor and use to determine that one or more gases have been detected. As described herein, the at least one processor may determine that one or more gases have been detected based on known reactions of one or more gases to materials similar to the sensing electrode 41 of the first sensor 20 under equivalent operating conditions. This information may be stored in the memory device (e.g., memory 16 shown in FIG. 1 and FIG. 4) within the apparatus 10, or may be supplied to the at least one processor from a remote server. The at least one processor may be further configured to, after determining whether one or more gases have been detected, power the second sensor. The method used may include having a portion of the at least one processor dedicated to the second sensor and only powering that section of the at least one processor when the first sensor has detected one or more gases. In some embodiments, hardware may be used to power the second sensor 22 with or without processing of the data from the first sensor 20 as described herein.

Now referring to FIG. 6, another example embodiment of the sensory assembly 24 is provided. As shown in this example embodiment, the first sensor 20 and the second sensor 22 may share the same housing 46. This may allow for more compact embodiments of the present invention. Unless stated otherwise, the embodiment of FIG. 6 may include the same components, materials, and operation as the components, materials, and operation of the embodiment of FIG. 5, and components with like names or reference numerals may operate in accordance with their description with respect to FIG. 5. The embodiment of FIG. 6 may optionally include a single electrolyte 48 and a is single counter electrode 49 to be provided to both the first sensor 20 and second sensor 22.

While in the same housing, the first sensor and second sensor may be defined in individual cavities as to not interfere with the other's operation. For example, the first sensing electrode 41 and the second sensing electrode 43 may be electrically isolated via a dividing wall in the housing. In some embodiments, the sensors 20, 22 may be oriented (e.g., by aligning the capillary openings) towards the same direction or area to capture substantially the same wises for analysis.

In some embodiments, the apparatus 10 may include two or more first sensors 20 and one or more second sensors 22 configured to improve detection and identification of the ambient gases. For example, sensors that detect both oxidizing and reducing gases may have their current responses cancel out if both an oxidizing and reducing gas are present. In some embodiments, a first first sensor 20 may be configured to detect oxidizing gases, and a second first sensor 20 may be configured to detect reducing gases. Either sensor may be configured to independently cause the second sensor 22 to power on according to any of the embodiments discussed herein.

In some embodiments, a single second sensor 22 may be configured to detect both oxidizing and reducing gases. In some embodiments, the responses of the second sensor 22 may not cancel when reducing and oxidizing gases are present because each voltage applied to the second sensor during the voltage scanning is configured to allow the sensor to detect a small subset of the nearby gases, and the range of voltages may be configured to span the sensing range of each first sensor (e.g., the first first sensor and second first sensor discussed above). In some embodiments, multiple second sensors may be used in parallel to scan a subset of the total detection range of the first sensors. In some embodiments, the amount of different voltage scans may be based on the number of possible gases detected (e.g., if only 7 gases may possibly be detected, 7 or more voltage measurements may be used). In some embodiments, the amount of different voltage scans may be greater than the number of possible gases detected. In some embodiments, a larger number of voltage scans relative to the possible number of gases may allow for the apparatus to capture and fit peaks to the gases present (e.g., as shown in FIG. 9, a large number of measurements may be made, up to 1000 measurements, to create a complete graph). In some embodiments, at least 5 different voltages may be used during the scanning.

Additional sensors, either detections sensors or identification sensors, may also be provided in the same housing as the first sensor and the second sensor, or in a housing is distinct from the first sensor and the second sensor. These additional sensors may use the single electrolyte and counter electrode provided for the first sensor and the second sensor, or may have additional electrolytes and/or counter electrodes.

Now referring to FIG. 7, another example gas diffusion sensor 700 is provided that may be used as either one or both of a first sensor 20 (a detection sensor) or second sensor 22 (an identification sensor) according to the embodiments discussed herein. The embodiments of FIG. 5 and FIG. 6 depict two-electrode gas diffusion sensors using a sensing electrode 41, 43 and counter electrode 49, 49a, 49b. In the embodiment shown in FIG. 7 a three-electrode embodiment is shown having a sensing electrode 74, counter electrode 49, and reference electrode 72. The sensor of FIG. 7 and operation thereof may be used in any of the sensor embodiments detailed herein. For example, in some embodiments using a microelectrode, the second sensor may be similar to the sensor of FIG. 7 with a microelectrode in the place of a sensing electrode.

As in the example embodiment of FIG. 7, the gas diffusion sensor 700 is an electrochemical sensor. The depicted sensor 700 includes a potentiostat 70 configured to control the potential of the sensing electrode 74 (e.g., control the power directed from the power source 18 shown in FIG. 4). The potentiostat 70 may be electrically connected to a sensing electrode 74, the reference electrode 72, and the counter electrode 49. In some embodiments, the potentiostat 70 may maintain a constant potential at the sensing electrode 74 with respect to the reference electrode 72 by adjusting the current at the counter electrode 49. The potentiostat 70 may also generate and output sensor data to the processor and other computing devices described herein. In some embodiments, a two-electrode potentiostat (e.g., a bipotentiostat) may be used to control two-electrode embodiments (e.g., the embodiments depicted in FIG. 5 and FIG. 6) in substantially the same manner.

The ambient gas may be allowed to enter the sensor through a capillary limited entry hole 42. The capillary limiting component of a sensor may be an integral part of the sensor housing or may be positioned proximate to the sensor in order to restrict the amount of gas that reaches the sensing components as described with respect to the capillaries 42a, 42b of FIG. 5 and FIG. 6. After the gas has entered the sensor housing it may enter the sensing electrode 74. The sensing electrode, as discussed above, may be selected from various materials based on the gases to be detected. An electrolyte 48 may be provided and may contain a reference electrode for facilitating control and regulation of the electric potential at the sensing electrode 74 and counter electrode 49. The counter electrode 49 is may also be provided.

In one example embodiment, the sensor is exposed to Hydrogen Sulfide ($H_2S$). In the example embodiment shown in FIG. 7, $H_2S$ gas enters into the sensor housing through the capillary limited entry hole 42. The gas then goes through an anodically charged sensing electrode where a reaction occurs to create Sulfuric Acid ($H_2SO_4$) and hydrogen ions ($H_2S+4H_2O>H_2SO_4+8H^++8e^-$). The sensing electrode in this example embodiment may be platinum and the electrolyte may be sulfuric acid. An opening in the reference electrode 72 may be provided to allow dissolved gases to pass to the counter electrode 49. The counter electrode may be cathodic in some embodiments. The counter electrode then may have a reaction with the free Oxygen and Hydrogen to create water ($2O_2+8H^++8e^->4H_2O$). The counter electrode then outputs the water, which may allow for zero net consumption of water. In some embodiments, ions, such as hydrogen ions, may be transferred from one electrode to another through the electrolyte, while electrons may flow through the external circuit.

As described above, FIG. 2 and FIG. 3 illustrate flowcharts of various aspects of an apparatus 10 and method according to example embodiments of the invention. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by the memory device 16 of a software development test platform employing an embodiment of the present invention and executed by the processing circuitry 12, the processor 14 or the like of the software development test platform. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method for determining a composition of one or more gases with a sensor assembly and at least one processor, the sensor assembly comprising a first gas sensor and a second gas sensor, the method comprising:
  causing the first gas sensor to be powered to detect a presence of one or more gases while the second gas sensor is unpowered;
  detecting, via the first gas sensor, the presence of the one or more gases while the second gas sensor is unpowered;
  in response to detecting the presence of the one or more gases, causing the second gas sensor to be powered;
  generating, via the second gas sensor, sensor data corresponding to at least one of the one or more gases by applying a plurality of voltages to the second gas sensor and receiving current measurements through the second gas sensor at each of the plurality of voltages; and
  identifying, via the at least one processor, the at least one of the one or more gases based on an analysis of the sensor data.

2. The method of claim 1 further comprising determining a quantity of total gases present based on first sensor data generated by the first gas sensor and determining proportions and identities of the one or more gases based on the sensor data generated by the second gas sensor.

3. The method of claim 2, wherein the identities of the at least one of the one or more gases are determined by comparing voltages at which second sensor response peaks occur with response peaks of at least one known gas.

4. The method of claim 2, further comprising combining, via the at least one processor, the quantity of total gases present determined from the first sensor data generated by the first gas sensor with the proportions and identities of the one or more gases determined from the sensor data generated by the second gas sensor to determine a total amount and identity of one or more of the detected gases.

5. The method of claim 1, wherein the second gas sensor has a surface area less than that of the first gas sensor.

6. The method of claim 1, further comprising a housing defining a limiting capillary proximate to at least one of the first gas sensor and the second gas sensor, wherein the limiting capillary is configured to limit a volume of one or more gases that the at least one of the first gas sensor or second gas sensor receives.

7. The method of claim 1, wherein detecting, via the first gas sensor, the presence of the one or more gases comprises applying a constant voltage to the first gas sensor and detecting a change in current through the first gas sensor.

8. The method of claim 1, wherein identifying, via the at least one processor, the at least one of the one or more gases based on the analysis of the sensor data comprises comparing the received current measurements at each of the plurality of voltages with known measurements of predetermined gases.

9. The method of claim 1, further comprising a second first sensor, wherein the second first sensor is configured to cause the second gas sensor to be powered in response to detecting the presence of a second one or more gases, and wherein the one or more gases are different than the second one or more gases.

10. An apparatus for determining a composition of one or more gases comprising a sensor assembly and at least one processor, the sensor assembly comprising a first gas sensor and a second gas sensor, the at least one processor having computer coded instructions therein, with the computer coded instructions configured to, when executed, cause the apparatus to:
  cause the first gas sensor to be powered to detect a presence of one or more gases while the second gas sensor is unpowered; detect, via the first gas sensor, the presence of the one or more gases while the second gas sensor is unpowered;
  in response to the detection of the presence of the one or more gases, cause the second gas sensor to be powered;
  generate, via the second gas sensor, sensor data corresponding to at least one of the one or more gases,
  wherein generating, via the second gas sensor, the sensor data corresponding to the at least one of the one or more gases comprises applying a plurality of voltages to the second gas sensor and receiving current measurements through the second gas sensor at each of the plurality of voltages; and
  identify, via the at least one processor, the at least one of the one or more gases based on an analysis of the sensor data.

11. The apparatus of claim 10 wherein the computer coded instructions are further configured to cause determine a quantity of total gases present based on first sensor data generated by the first gas sensor and determine proportions and identities of the one or more gases based on the sensor data generated by the second gas sensor, wherein the identities of the at least one of the one or more gases are determined by comparing voltages at which second sensor response peaks occur with response peaks of at least one known gas.

12. The apparatus of claim 11, wherein the computer coded instructions are further configured to cause the apparatus to combine the quantity of total gases present determined from the first sensor data captured by the first gas sensor with the proportions and identities of the one or more gases determined from the sensor data generated by the second gas sensor to determine a total amount and identity of one or more of the detected gases.

13. The apparatus of claim 10, wherein the second gas sensor has a surface area less than that of the first gas sensor.

14. The apparatus of claim 10, further comprising a housing defining a limiting capillary proximate to at least one of the first gas sensor and the second gas sensor, wherein the limiting capillary is configured to limit a volume of one or more gases that the at least one of the first gas sensor or second gas sensor receives.

15. The apparatus of claim 10, wherein detecting, via the first gas sensor, the presence of the one or more gases comprises applying a constant voltage to the first gas sensor and detecting a change in current through the first gas sensor.

16. The apparatus of claim 10, wherein identifying, via the at least one processor, the at least one of the one or more gases based on the analysis of the sensor data comprises comparing the received current measurements at each of the plurality of voltages with known measurements of predetermined gases.

17. The apparatus of claim 10, further comprising a second first sensor, wherein the second first sensor is configured to cause the second gas sensor to be powered in response to detecting the presence of a second one or more gases, and wherein the one or more gases are different than the second one or more gases.

18. The apparatus of claim 10, wherein the second gas sensor is configured to generate the sensor data for each gas capable of detection by the first gas sensor.

* * * * *